United States Patent
Grubb et al.

(10) Patent No.: US 6,380,178 B1
(45) Date of Patent: Apr. 30, 2002

(54) CYCLIC REGIMENS USING CYCLOCARBAMATE AND CYCLIC AMIDE DERIVATIVES

(75) Inventors: Gary S. Grubb, Newtown Square; Arthur A. Santilli, Havertown; Andrew Q. Viet, Upper Darby; Puwen Zhang, Audubon; Andrew Fensome, Wayne, all of PA (US); Jay E. Wrobel, Lawrenceville, NJ (US); James P. Edwards, San Diego, CA (US); Todd K. Jones, Solana Beach, CA (US); Christopher M. Tegley, Thousand Oaks, CA (US); Lin Zhi, San Diego, CA (US)

(73) Assignees: American Home Products Corporation, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/552,545

(22) Filed: Apr. 19, 2000

Related U.S. Application Data

(60) Provisional application No. 60/198,246, filed on May 4, 1999.

(51) Int. Cl.[7] .................. A61K 31/56; A61K 31/535; A61K 31/445; A61K 31/40
(52) U.S. Cl. ................ 514/171; 514/230.5; 514/321; 514/414
(58) Field of Search .................. 514/171, 230.5, 514/321, 414

(56) References Cited

U.S. PATENT DOCUMENTS

| | | | |
|---|---|---|---|
| 3,635,964 A | 1/1972 | Skorcz et al. | 260/247.1 |
| 3,917,592 A | 11/1975 | Kobzina | 260/244 |
| 4,093,730 A | 6/1978 | Butti | 424/270 |
| 4,440,785 A | 4/1984 | Walsh | 424/317 |
| 4,666,613 A | 5/1987 | Kubla et al. | 514/259 |
| 4,670,566 A | 6/1987 | Walsh | 548/485 |
| 4,721,721 A | 1/1988 | Kuhla | 514/312 |
| 4,822,794 A | 4/1989 | Spada | 514/230 |
| 4,831,027 A | 5/1989 | Narr et al. | 514/212 |

(List continued on next page.)

FOREIGN PATENT DOCUMENTS

| | | |
|---|---|---|
| DE | 3633861 | 4/1988 |
| DE | 43 30 234 | 3/1995 |
| DE | 43 44 463 | 6/1995 |
| EP | 022317 | 1/1981 |
| EP | 0 208 510 | 1/1987 |
| EP | 311135 | 4/1989 |
| EP | 385850 | 9/1990 |
| EP | 483077 | 9/1991 |

(List continued on next page.)

OTHER PUBLICATIONS

R.M. Evans, "The Steroid and Thyroid Hormone Receptor Superfamily", *Science*, 240:889 (May 13, 1988).
A. Ulmann et al., "Clinical Uses of Mifepristone (MFP)", *Ann. N.Y. Acad. Sci.*, 261:248 (Jun. 12, 1995).
R. Kekkonen et al., "Sequential Regiment of the Antiprogesterone RU486 and Synthetic Progestin for Contraception", *Fertility and Sterility*, 60(4):610 (Oct. 1993).
K. Horwitz et al., "Progestin, Progesterone Receptors, and Breast Cancer", "Horm. Cancer", publisher: Birkhaeuser, Boston, Mass., ed. Vedeckis, pp. 283–306 (1996) abstract only.
A. A. Murphy et al., "Regression of Uterine Leiomyomata in Response to the Antiprogesterone RU 486", *J. Clin. Endo. Metab.*, 76(2):513 (Feb. 1993).
L. M. Kettel et al., "Endocrine Responses to Long–Term Administration of the Antiprogesterone RU486 in Patients with Pelvic Endometriosis", *Fertility and Sterility*, 56(3):402 (Sep. 1991).
H. Michna et al., "Differentiation Therapy with Progesterone Antagonists", *Ann. N.Y. Acad. Sci.*, 761:224 (Jun. 1995).
L. Zhi et al., "5–Aryl–1,2–Dihydrochromeno[3,4–f]quinolines: A Novel Class of Nonsteroidal Human Progesterone Receptor Agonists", *J. Med. Chem.*, 41(3):291 (Oct. 22, 1998).

(List continued on next page.)

*Primary Examiner*—Minna Moezie
*Assistant Examiner*—San-ming Hui
(74) *Attorney, Agent, or Firm*—Howson and Howson

(57) ABSTRACT

This invention relates to cyclic combination therapies and regimens utilizing, in combination with progestins, substituted indoline derivative compounds which are antagonists of the progesterone receptor having the general structure:

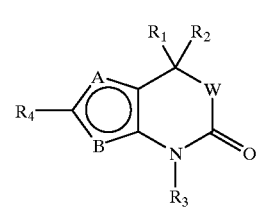

where A and B are independent substituents selected from S, CH or N; provided that when A is S, B is CH or N; and when B is S, A is CH or N; and A and B cannot both be CH; and when A and B both equal N, one N may be optionally substituted with an $C_1$ to $C_6$ alkyl group; $R_1$ and $R_2$ are independent substituents selected from the group of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$; or $R^1$ and $R^2$ are fused to form optionally substituted 3 to 8 membered spirocyclic alkyl, alkenyl or heterocyclic ring, the heterocyclic ring containing one to three heteroatoms selected from the group of O, S and N; or pharmaceutically useful salts thereof. These methods of treatment may be used for contraception.

13 Claims, No Drawings

U.S. PATENT DOCUMENTS

| | | | |
|---|---|---|---|
| 4,853,473 A | 8/1989 | Fischer et al. | 549/326 |
| 5,007,952 A | 4/1991 | Kume et al. | 71/73 |
| 5,171,851 A | 12/1992 | Kim et al. | 544/50 |
| 5,414,088 A | 5/1995 | Von Der Saal et al. | 546/158 |
| 5,453,516 A | 9/1995 | Fischer et al. | 548/543 |
| 5,475,020 A | 12/1995 | Johnson et al. | 548/466 |
| 5,521,166 A | 5/1996 | Grubb | 514/170 |
| 5,681,817 A | 10/1997 | Hodgen et al. | 514/12 |
| 5,688,808 A | 11/1997 | Jones et al. | 514/285 |
| 5,688,810 A | 11/1997 | Jones et al. | 514/311 |
| 5,693,646 A | 12/1997 | Jones et al. | 514/285 |
| 5,693,647 A | 12/1997 | Jones et al. | 514/285 |
| 5,696,127 A | 12/1997 | Jones et al. | 514/285 |
| 5,696,130 A | 12/1997 | Jones et al. | 514/291 |
| 5,696,133 A | 12/1997 | Pooley et al. | 514/314 |
| 5,719,136 A | 2/1998 | Chwalisz et al. | 514/170 |
| 5,733,902 A | 3/1998 | Schneider | 514/177 |
| 5,808,139 A | 9/1998 | Pathirana | 560/138 |
| 5,874,430 A | 2/1999 | Christ | 514/229.8 |
| 6,077,840 A | 6/2000 | Kurihara | 514/232.8 |

FOREIGN PATENT DOCUMENTS

| | | |
|---|---|---|
| EP | 454330 | 10/1991 |
| EP | 0 535 529 | 9/1992 |
| EP | 510235 | 10/1992 |
| EP | 947 507 | 10/1999 |
| EP | 978 279 | 2/2000 |
| JP | 63112584 | 5/1988 |
| WO | WO 86/03749 | 7/1986 |
| WO | WO 91/04974 | 4/1991 |
| WO | WO 91/06545 | 5/1991 |
| WO | WO 93/12085 | 6/1993 |
| WO | WO 94/14434 | 7/1994 |
| WO | WO 94/29272 | 12/1994 |
| WO | WO 95/11013 | 4/1995 |
| WO | WO 95/20389 | 8/1995 |
| WO | WO 95/20972 | 8/1995 |
| WO | WO 95/33746 | 12/1995 |
| WO | WO 96/15794 | 5/1996 |
| WO | WO 96/19458 | 6/1996 |
| WO | WO 96/19997 | 7/1996 |
| WO | WO 97/13767 | 4/1997 |
| WO | WO 97/49407 | 12/1997 |
| WO | WO 98/14436 | 4/1998 |
| WO | WO 98/27059 | 6/1998 |
| WO | WO 98/55116 | 12/1998 |
| WO | WO 99/10325 | 3/1999 |
| WO | WO 99/11264 | 3/1999 |
| WO | WO 99/15500 | 4/1999 |
| WO | WO 99/44608 | 9/1999 |

OTHER PUBLICATIONS

D. W. Combs et al., "Nonsteroidal Progesterone Receptor Ligands. 2. High–Affinity Ligands with Selectivity for Bone Cell Progesterone Receptors", *J. Med. Chem.*, 38:4880 (Dec. 8, 1995).

K. L. Perlman et al., "20–Oxopregnacalciferols: Vitamin D Compounds that Bind the Progesterone Receptor", *Tet. Letters*, 35(15):2295 (1994).

L. G. Hamann et al., "Synthesis and Biological Activity of Novel Nonsteroidal Progesterone Receptor Antagonists", *Ann. N.Y. Acad. Sci.*, 761:383 (Jun. 12, 1995).

R. H. K. Chen et al., "Synthesis and SAR of a Novel Series of Spirobenzothlzaepine Derivatives with Antiprogestin Activity", POI–37, 16$^{th}$ Int. Cong. Het. Chem., Montana (1997).

B. Narr et al., "Preparation, Testing, and Formulation of Imidazobenzoxazinones as Cardiotonics", *Chemical Abstracts*, 109:22973 (1988).

R. J. Hartmann et al., "Effects of Brofoxine, A New Anxiolytic on Experimentally Induced Conflict in Rats", *Proc West. Pharmacol. Soc.*, 21:51–55 (1978).

B. Singh et al., "Novel cAMP PDE III Inhibitor: Imidazo [4,5–b]pyridin–2(3H)–ones and Thiazolo[4,5–b] pyridin–2(3H)–ones and Their Analogs", *J. Med. Chem.*, 37:248 (Jan. 21, 1994).

A. Andreani et al., "Potential Antitumor Agents XVII (1). Cytotoxic Agents from Indole Derivatives and Their Intermediates", *Acta. Pharm. Nord.*, 2(6):407 (1990).

Sakata et al., "Silver Halide Photographic Materials Useful for Platemaking", *Chemical Abstracts*, 123:301431 (1993).

P. Pflegel et al., "Polarografie con 7–Chlor–5–phenyl–2–thioxo–1H–2,3–dihydro–1,3,4–benzotriazepinen", *Pharmazie*, 37(10): 714–717 (1982).

E. I. Barengolts et al., "Progesterone Antagonist RU 486 Has Bone–Sparing Effects in Ovariectomized Rats", *Bone*, 17(1):21 (Jul. 1995).

E. V. Gromachevskaya et al., "Studies of 4H–3, 1–Benzoxazines", *Chem. Heterocycl. Cmpds.* 33(10):1209–1214 (1997).

D. Chiarino et al., "2, 1– Benzisothiazoline 2, 2–Dioxide and Derivatives", *J. Heterocycl. Chem.*, 23(6):1645–1649 (Nov.– Dec. 1986).

A. Turck et al., "On the Metabolism of 3–Substituted and 3,6–Disubstituted Pyridazines", *Tetrahedron*, 49(3):599–606 (1993).

V. Kumar et al., "Synthesis of 7–Azaindole and 7–Azaoxindole Derivatives through a Palladium–Catalyzed Cross–Coupling Reaction", *J. Org. Chem.*, 57(25):6995–6998 (1992).

P. Canonne et al., "Spirocyclization of 1–(o–Aminophenyl) cycloalkanols and 1–(2'–Amino–3'–pyridinyl)cycloalkanols", *J. Heterocyclic Chem.*, 26:113 (Jan.–Feb. 1989).

M–C. Forest et al., "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", *J. Med. Chem.*, 35:163–172 (Jan. 1992).

D. W. Combs et al., "Heteroatom Analogues of Bemoradan: Chemistry and Cardiotonic Activity of 1, 4–Benzothiazinylpyridazinones", *J. Med. Chem.*, 35:172–176 (Jan. 1992).

Kurihari et al., "Synthesis of (±)–PF1092A, B, and C; New Nonsteroidal Progesterone Receptor Ligands", *J. Antibiotics*, 50(4):360 (Apr. 1997).

A. Kende et al., "Regioselective C–3 Alkylation of Oxindole Dianion", *Synth. Commun.* 12(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", *J. Med. Chem.*, 37:2347–2444 (Jul. 22, 1994).

J. P. Edwards et al., "5–Aryl–1,2–Dihydro–5H–Chromeno [3,4–f]Quinolines as Potent, Orally Active, Nonsteroidal Progesterone Receptor Agonists: The Effect of D–Ring Substituents", *J. Med. Chem.*, 41:303–310 (Jan. 29, 1998).

Derwent WPI abstract, "New Imidazo–Pyridine Derivatives—Useful as Platelet Agglutination Inhibitor, Antiallergic, Antiinflammatory Sedative, Cardiac, and Cardiovascular Vasodilators", JP 63112584 (May 1988).

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850 (Sep. 1990).

Derwent WPI abstract, F. Arndt et al., "New Heterocycle substituted Benzo–Fused Azine and Azole Derivatives—Useful as Selective Herbicides for Pre or Post–Emergence Application", EP 311135 (Apr. 1989).

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

Mamaev, V.P., et al., "Synthesis of 4H–Thieno [3,2–B] Pyrrol–5(6H)–One" Bulletin of the Academy of Sciences on the USSR. Division of Chemical Science, US, Consultants Bureau. New York. vol. 9, p. 1549–1553, 1966.

Derwent WPI Abstract, Chwalisz, K., et al. "Female Contraceptive Method Comprises Gestation Treatment with Intermittent Progesterone Antagonist Administration.", DE 4,330,234. (Mar. 1995).

Derwent WPI Abstract, Chwalisz, K., et al. "Contraceptive Pack for Implantation Inhibition—Contains Competitive Progesterone Antagonist and Gestagen for Sequential Oral Administration.", DE 4,344,463. (Jun. 1995).

Kolasa, K., et al., "Preliminary Pharmacological Studies of the Central Action of Phenyl and Piperidinomethyl Derivatives of 2–Benzoxazolone." *Chemical Abstracts,* vol. 99, No. 1, Abst. No. 157a, Jul. 4, 1983.

Meanwell N.A., et al., "Regiospecific Functionalization of 1,3–dihydro–2H–Benzimidazol–2–One and Structurally Related Cyclic Urea Derivatives" *J. Organic Chem.,* 60(6): 1565–82 (Mar. 24, 1995).

Singh, B., et al., "An Efficient and Novel Synthesis of Fused Thiazol–2(3H)–ones" *Heterocycles,* 36(1): 133–134, p. 136, compounds 16a, 18a, Jan. 1993.

Vernin, G., et al., "Etude Dans la Serie des Radicaux Heterocycliques. Partie XV. Decomposition aprotique de 1' amino–6–ethyl–2–benzothiazole dans des substrats aromatiques et heteroaromatiques: preparation des mesityl–6– et furyl–6–ethyl–2–benzothiazoles, des sels quaternaires et des spiropyrannes correspondants" *Helvetica Chimica Acta,* 62(1/3):21–30 Jan. 24, 1979.

CYCLIC REGIMENS USING CYCLOCARBAMATE AND CYCLIC AMIDE DERIVATIVES

CROSS-REFERENCE TO RELATED APPLICATIONS

This application claims the benefit of the priority of U.S. patent application Ser. No. 09/305,007, converted to provisional application Serial No. 60/198,246 filed May 4, 1999.

FIELD OF THE INVENTION

This invention relates to regimens of administering compounds which are antagonists of the progesterone receptor in combination with a progestin, an estrogen, or both.

BACKGROUND OF THE INVENTION

Intracellular receptors (IR) form a class of structurally related genetic regulators known as "ligand dependent transcription factors" (R. M. Evans, *Science*, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex then translocates to the nucleus of the cell where it binds to a specific gene or genes present in the cell's DNA. Once bound to a specific DNA sequence the complex modulates the production of the mRNA and protein encoded by that gene.

A compound that binds to an IR and mimics the action of the natural hormone is termed an agonist, whilst a compound which inhibits the effect of the hormone is an antagonist. PR agonists (natural and synthetic) are known to play an important role in the health of women. PR agonists are used in birth control formulations, typically in the presence of an ER agonist. ER agonists are used to treat the symptoms of menopause, but have been associated with a proliferative effect on the uterus (in non-hysterectomized women) which can lead to an increased risk of uterine cancers. Co-administration of a PR agonist reduces/ablates that risk. PR antagonists may also be used in contraception. In this context they may be administered alone (Ulmann, et al, *Ann. N.Y. Acad. Sci.*, 261, 248, 1995), in combination with a PR agonist (Kekkonen, et al, *Fertility and Sterility*, 60, 610, 1993) or in combination with a partial ER antagonist such as tamoxifen (WO 96/19997 A1, Jul. 4, 1996).

PR antagonists may also be useful for the treatment of hormone dependent breast cancers (Horwitz, et al, *Horm. Cancer*, 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, *J. Clin. Endo. Metab.*, 76, 513, 1993) and endometriosis (Kettel, et al, *Fertility and Sterility*, 56, 402, 1991).

PR antagonists may also be useful in hormone replacement therapy for post menopausal patients in combination with a partial ER antagonist such as tamoxifen (U.S. Pat. No. 5,719,136). PR antagonists such as Mifepristone have also been shown to have bone sparing effects in rodents, and as such may be useful in the treatment of osteoporosis associated with the menopause (Barengolts, et al, *Bone*, 17, 21, 1995). PR antagonists, such as mifepristone and onapristone, have been shown to be effective in a model of hormone dependent prostate cancer, which may indicate their utility in the treatment of this condition in men (Michna, et al, *Ann. N.Y. Acad. Sci.*, 761, 224, 1995).

Jones, et al, (U.S. Pat. No. 5,688,810) described the PR antagonist dihydroquinoline 1.

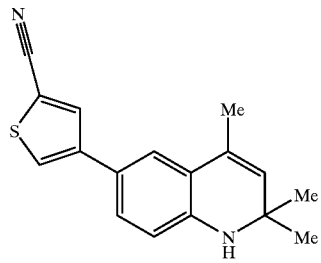

Jones, et al, described the enol ether 2 (U.S. Pat. No. 5,693,646) as a PR ligand.

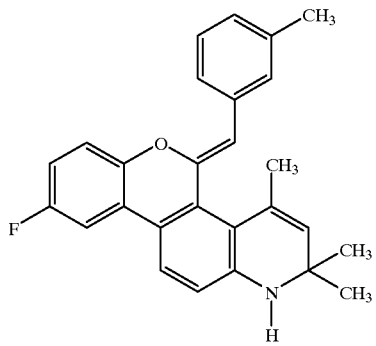

Jones, et al, described compound 3 (U.S. Pat. No. 5,696,127) as a PR ligand.

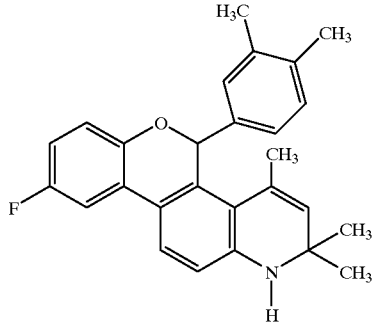

Zhi, et al, described lactones 4, 5 and 6 as PR antagonists (J. Med. Chem, 41, 291, 1998).

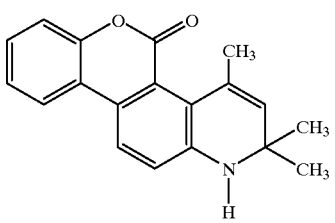

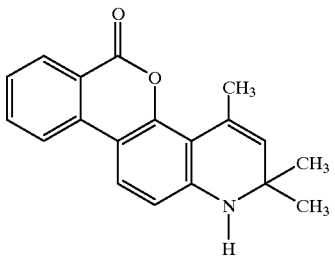

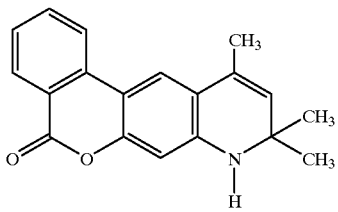

Zhi, et al, described the ether 7 as a PR antagonist (*J. Med. Chem*, 41, 291, 1998).

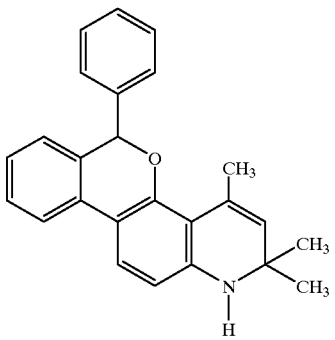

Combs, et al., disclosed the amide 8 as a ligand for the PR (*J. Med. Chem.*, 38, 4880, 1995).

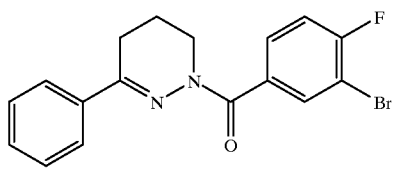

Perlman et. al., described the vitamin D analog 9 as a PR ligand (*Tet. Letters,* 35, 2295, 1994).

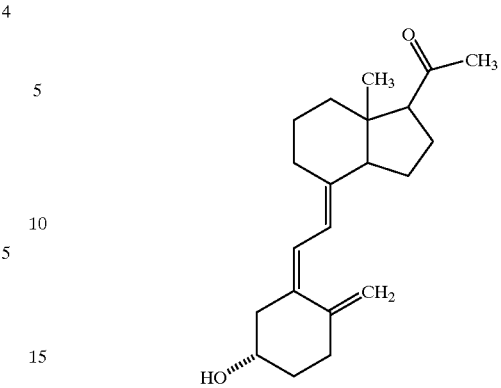

Hamann, et al, described the PR antagonist 10 (*Ann. N.Y. Acad. Sci.,* 761, 383, 1995).

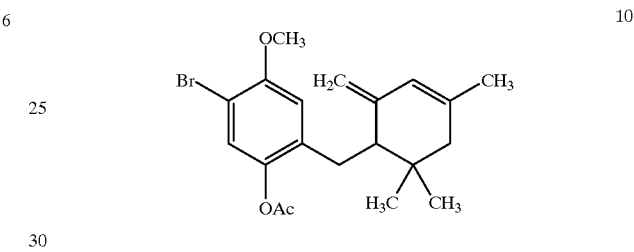

Chen, et al, described the PR antagonist 11 (Chen, et al, POI-37, 16th Int. Cong. Het. Chem, Montana, 1997).

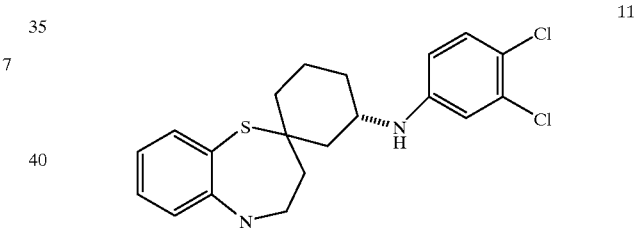

Kurihari, et. al., described the PR ligand 12 (*J. Antibiotics,* 50, 360, 1997).

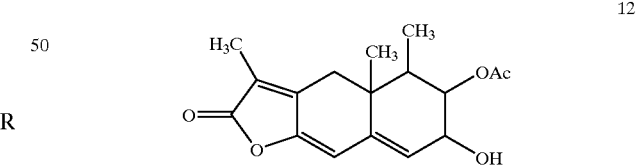

U.S. Pat. No. 5,521,166 (Grubb) teaches cyclophasic hormonal regimens comprising an antiprogestin and a progestin wherein the progestin is administered in the alternating presence and absence of an antiprogestin. The disclosed regimens also provide for use of an estrogen for a period of from 2–4 days to prevent breakthrough bleeding.

DESCRIPTION OF THE INVENTION

This invention provides combination therapies and dosing regimens utilizing antiprogestational agents in combination with one or more progestational agents. This invention further provides methods of treatment and dosing regimens further utilizing in combination with these antiprogestins and progestins, an estrogen, such as ethinyl estradiol.

These regimens and combinations may be administered to a mammal to induce contraception or for the treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake. The uses herein for the treatment and/or prevention of the conditions or diseases described above includes the continuous administration or periodic discontinuation of administration of the invention to allow for minimization of effect dose or minimization of side effects or cyclic menstrual bleeding.

The use of this invention for contraception includes administration, preferably orally, to a female of child bearing age an antiprogestin in combination with an estrogen or progestin or both. These administration regimens are preferably carried out over 28 consecutive days, with a terminal portion of the cycle containing administration of no progestins, estrogens or anti-progestins.

The progestins of these combinations may be administered alone or in combination with an estrogen for the first 14 to 24 days of the cycle, the progestins being administered at a dosage range equal in progestational activity to about 35 $\mu$g to about 150 $\mu$g levonorgestrel per day, preferably equal in activity to from about 35 $\mu$g to about 100 $\mu$g levonorgestrel per day. An antiprogestin may then be administered alone or in combination with an estrogen for a period of 1 to 11 days to begin on any cycle day between day 14 and 24. The anti-progestin in these combinations may be administered at a dose of from about 2$\mu$g to about 50 $\mu$g per day and the estrogen may be administered at a dose of from about 10 $\mu$g to about 35 $\mu$g per day. In an oral administration, a package or kit containing 28 tablets will include a placebo tablet on those days when the antiprogestin or progestin or estrogen is not administered.

In a preferred embodiment of this invention, the progestins of this invention may be administered alone or in combination with estrogen for the initial 18 to 21 days of a 28-day cycle, followed by administration of an antiprogestin, alone or in combination with an estrogen, for from 1 to 7 days.

The estrogen to be used in the combinations and formulations of this invention is preferably ethinyl estradiol.

Progestational agents useful with this invention include, but are not limited to, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Among the preferred progestins for use in the combinations of this invention are levonorgestrel, gestodene and trimegestone.

Examples of orally administered regimens of this invention over a 28 day cycle include administration of a progestational agent solely for the first 21 days at a daily dose equal in progestational activity to from about 35 to about 100 $\mu$g of levonorgestrel. An antiprogestin compound of this invention may then be administered at a daily dose of from about 2 to 50 mg from day 22 to day 24, followed by no administration or administration of a placebo for days 25 to 28. It is most preferred that the daily dosages of each relevant active ingredient be incorporated into a combined, single daily dosage unit, totaling 28 daily units per 28-day cycle.

In another regimen, a progestational agent may be coadministered for the first 21 days at a daily dose equal in progestational activity to from about 35 to about 150 $\mu$g levonorgestrel, preferably equal in activity to from about 35 to about 100 $\mu$g levonorgestrel, with an estrogen, such as ethinyl estradiol, at a daily dose range of from about 10 to about 35 $\mu$g. This may be followed as described above with an antiprogestin administered at a daily dose of from about 2 to 50 mg from day 22 to day 24, followed by no administration or administration of a placebo for days 25 to 28.

Still another regimen within the scope of this invention will include coadministration from days 1 to 21 of a progestational agent, the progestational agent, preferably levonorgestrel, being administered at a daily dose equal in progestational activity to from about 35 to about 100 $\mu$g levonorgestrel, and an estrogen, such as ethinyl estradiol, at a daily dose range of from about 10 to about 35 $\mu$g. This will be followed on days 22 to 24 by coadministration of an antiprogestin (2 to 50 mg/day) and an estrogen, such as ethinyl estradiol, at a daily dose of from about 10 to about 35 $\mu$g. From day 25 to day 28, this regimen may be followed by no administration or administration of a placebo.

This invention also kits or packages of pharmaceutical formulations designed for use in the regimens described herein. These kits are preferably designed for daily oral administration over a 28-day cycle, preferably for one oral administration per day, and organized so as to indicate a single oral formulation or combination of oral formulations to be taken on each day of the 28-day cycle. Preferably each kit will include oral tablets to be taken on each the days specified, preferably one oral tablet will contain each of the combined daily dosages indicated.

According to the regimens described above, one 28-day kit may comprise:

a) an initial phase of from 14 to 21 daily dosage units of a progestational agent equal in progestational activity to about 35 to about 150 $\mu$g levonorgestrel, preferably equal in progestational activity to about 35 to about 100 $\mu$g levonorgestrel;

b) a second phase of from 1 to 11 daily dosage units of an antiprogestin compound of this invention, each daily dosage unit containing an antiprogestin compound at a daily dosage of from about 2 to 50 mg; and c) optionally, a third phase of an orally and pharmaceutically acceptable placebo for the remaining days of the cycle in which no antiprogestin, progestin or estrogen is administered.

A preferred embodiment of this kit may comprise:

a) an initial phase of 21 daily dosage units of a progestational agent equal in progestational activity to about 35 to about 150 $\mu$g levonorgestrel, preferably equal in progestational activity to about 35 to about 100 $\mu$g levonorgestrel;

b) a second phase of 3 daily dosage units for days 22 to 24 of an antiprogestin compound of this invention, each daily dosage unit containing an antiprogestin compound at a daily dosage of from about 2 to 50 mg; and c) optionally, a third phase of 4 daily units of an orally and pharmaceutically acceptable placebo for each of days 25 to 28.

Another 28-day cycle packaging regimen or kit of this invention comprises:

a) a first phase of from 18 to 21 daily dosage units of a progestational agent equal in progestational activity to about 35 to about 150 µg levonorgestrel, preferably equal in activity to from about 35 to about 100 µg levonorgestrel, and, as an estrogen, ethinyl estradiol at a daily dose range of from about 10 to about 35 µg; and b) a second phase of from 1 to 7 daily dosage units of an antiprogestin of this invention at a daily dose of from about 2 to 50 mg; and c) optionally, an orally and pharmaceutically acceptable placebo for each of the remaining 0–9 days in the 28-day cycle in which no progestational agent, estrogen or antiprogestin is administered.

A preferred embodiment of the kit described above may comprise:

a) a first phase of 21 daily dosage units of a progestational agent equal in progestational activity to about 35 to about 150 µg levonorgestrel, preferably equal in activity to from about 35 to about 100 µg levonorgestrel, and, as an estrogen, ethinyl estradiol at a daily dose range of from about 10 to about 35 µg; and b) a second phase of 3 daily dosage units for days 22 to 24 of an antiprogestin administered at a daily dose of from about 2 to 50 mg; and c) optionally, a third phase of 4 daily dose units of an orally and pharmaceutically acceptable placebo for each of days 25 to 28.

A further 28-day packaged regimen or kit of this invention comprises:

a) a first phase of from 18 to 21 daily dosage units, each containing a progestational agent of this invention at a daily dose equal in progestational activity to about 35 to about 150 µg levonorgestrel, preferably equal in activity to from about 35 to about 100 µg levonorgestrel, and ethinyl estradiol at a daily dose range of from about 10 to about 35 µg;

b) a second phase of from 1 to 7 daily dose units, each daily dose unit containing an antiprogestin of this invention at a concentration of from 2 to 50 mg; and ethinyl estradiol at a concentration of from about 10 to about 35 µg; and c) optionally, an orally and pharmaceutically acceptable placebo for each of the remaining 0–9 days in the 28-day cycle in which no progestational agent, estrogen or antiprogestin is administered.

A preferred embodiment of the package or kit just described comprises:

a) a first phase of 21 daily dosage units, each containing a progestational agent of this invention at a daily dose equal in progestational activity to about 35 to about 150 µg levonorgestrel, preferably from about 35 to about 100 µg levonorgestrel, and ethinyl estradiol at a daily dose range of from about 10 to about 35 µg;

b) a second phase of 3 daily dose units for days 22 to 24, each dose unit containing an antiprogestin of this invention at a concentration of from 2 to 50 mg; and ethinyl estradiol at a concentration of from about 10 to about 35 µg; and c) optionally, a third phase of 4 daily units of an orally and pharmaceutically acceptable placebo for each of days 25 to 28.

In each of the regimens and kits just described, it is preferred that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also preferred that the kits contain the placebo described for the final days of the cycle. It is further preferred that each package or kit comprise a pharmaceutically acceptable package having indicators for each day of the 28-day cycle, such as a labeled blister package or dial dispenser packages known in the art.

In this disclosure, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

Compounds of this invention which may be used as the anti-progestational agents in the kits, methods and regimens herein include those of the Formula 1:

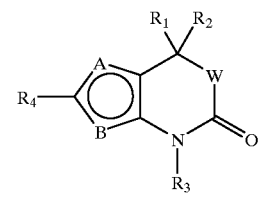

wherein:
A and B are independent substituents selected from S, CH or N;
  Provided that when A is S, B is CH or N; provided that when B is S, A is CH or N;
  and A and B cannot both be CH;
  and when A and B both equal N, one N may be optionally substituted with an $C_1$ to $C_6$ alkyl group;
  $R_1$ and $R_2$ are independent substituents selected from the group of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^B COR^A$;
  or $R^1$ and $R^2$ are fused to form:
    a) an optionally substituted 3 to 8 membered spirocyclic alkyl ring, preferably a 3 to 6 membered spirocyclic alkyl ring; or
    b) an optionally substituted 3 to 8 membered spirocyclic alkenyl ring, preferably a 3 to 6 membered spirocyclic alkenyl ring; or
    c) an optionally substituted 3 to 8 membered spirocyclic ring containing one to three heteroatoms selected from O, S and N, preferably a 3 to 6 membered spirocyclic ring containing one to three heteroatoms;
  $R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
  $R^B$ is H, $C_1$ to $C_3$ alkyl, or substituted $C_1$ to $C_3$ alkyl;
  $R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, or $COR^C$;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is a trisubstituted benzene ring containing the substituents X, Y and Z as shown below,

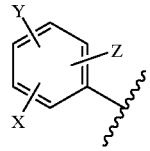

X is selected from halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl $NO_2$, $C_1$ to $C_3$ perfluoroalkyl, 5 or 6 membered heterocyclic ring containing 1 to 3 heteroatoms, $COR^D$, $OCOR^D$, or $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent independently selected from H, halogen, CN, $NO_2$, $C_1$ to $C_3$ alkoxy, $C_1$ to $C_3$ alkyl, or $C_1$ to $C_3$ thioalkyl; or $R^4$ is a five or six membered ring with 1, 2, or 3 heteroatoms from the group including O S, SO, $SO_2$ or $NR^5$ and containing one or two independent substituents from the group including H, halogen, CN, $NO_2$ and $C_1$ to $C_3$ alkyl, $C_1$ to $C_3$ alkoxy, $C_1$ to $C_3$ aminoalkyl, $COR^F$, or $NR^GCOR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^5$ is H, or $C_1$ to $C_3$ alkyl;

W is O or a chemical bond or a pharmaceutically acceptable salt thereof.

Among the preferred anti-progestational compounds for use with this invention are those of Formula I wherein:

A and B are independent substituents S, CH or N, provided that when A is S, B is CH or N; and
when B is S, A is CH or N; and
A and B cannot both be CH; and
when A and B both equal N, one N may be optionally substituted with an $C_1$ to $C_6$ alkyl group;

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkenyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

or $R^1$ and $R^2$ are fused to form:
a) an optionally substituted 3 to 8 membered spirocyclic alkyl ring; or
b) an optionally substituted 3 to 8 membered spirocyclic alkenyl ring; or
c) an optionally substituted 3 to 8 membered spirocyclic ring containing one to three heteroatoms selected from the group of O, S and N;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, or substituted alkynyl, or $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is a trisubstituted benzene ring containing the substituents X, Y and Z as shown below:

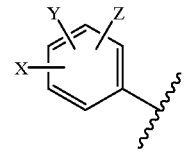

X is taken from the group including halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5-membered heterocyclic ring containing 1 to 3 heteroatoms, $COR^D$, $OCOR^D$, or $NR^ECOR^D$;

$R^D$ is H, $C_1$ to $C_3$ alkyl, substituted $C_1$ to $C_3$ alkyl, aryl, substituted &yl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents taken from the group including H, halogen, CN, $NO_2$, $C_1$ to $C_3$ alkoxy, $C_1$ to $C_3$ alkyl, or $C_1$ to $C_3$ thioalkyl; or $R^4$ is a five or six membered ring with 1, 2, or 3 heteroatoms from the group including O S, SO, $SO_2$ or $NR^5$ and containing one or two independent substituents from the group including H, halogen, CN, $NO_2$ and $C_1$ to $C_3$ alkyl, or $C_1$ to $C_3$ alkoxy;

$R^5$ is H or $C_1$ to $C_3$ alkyl;

W is O or a chemical bond or a pharmaceutically acceptable salt thereof.

Further preferred progesterone receptor antagonists are those of Formula I wherein:

A and B are independent substituents from the group including S, CH or N;
provided that when A is S, B is CH or N; and
when B is S, A is CH or N; and
A and B cannot both be CH;
$R^1=R^2$ and are selected from the group which includes $C_1$ to $C_3$ alkyl, substituted $C_1$ to $C_3$ alkyl, or spirocyclic alkyl constructed by fusing $R^1$ and $R^2$ to form a 3 to 6 membered spirocyclic ring;

$R^3$ is H, OH, $NH_2$, $C_1$ to $C_6$ alkyl, substituted $C_1$ to $C_6$ alkyl, or $COR^C$;

$R^C$ is H, $C_1$ to $C_4$ alkyl, or $C_1$ to $C_4$ alkoxy;

$R^4$ is a disubstituted benzene ring containing the substituents X and Y as shown below:

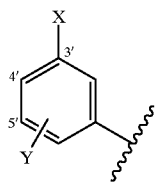

X is selected from the group including halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkyl;

Y is a substituent on the 4' or 5' position selected from the group of H, halogen, CN, $NO_2$, $C_1$ to $C_3$ alkoxy, $C_1$ to $C_4$ alkyl, or $C_1$ to $C_3$ thioalkyl; or $R^4$ is a five membered ring with the structure shown below:

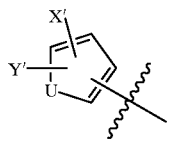

U is O, S, or $NR^5$;
$R^5$ is H, or $C_1$ to $C_3$ alkyl, or $C_1$ to $C_4$ $CO_2$alkyl;
X' is selected from halogen, CN, $NO_2$, $C_1$ to $C_3$ alkyl or $C_1$ to $C_3$ alkoxy;
Y' is H or $C_1$ to $C_4$alkyl; or
$R^4$ is a six membered ring with the structure:

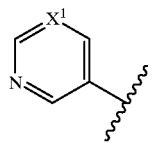

$X^1$ is N or $CX^2$;
$X^2$ is halogen, CN or $NO_2$;
W is O or a chemical bond; or a pharmaceutically acceptable salt thereof.

The anti-progestational compounds of this invention may contain an asymmetric carbon atom and some of the compounds of this invention may contain one or more asymmetric centers and may thus give rise to optical isomers and diastereomers. While shown without respect to stereochemistry in Formula I, II, and III, the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having from one to 8 carbon atoms, preferably from 1 to 6 carbon atoms; "alkenyl" is intended to include both straight- and branched-chain alkyl group having from 2 to 8 carbon atoms, preferably 2 to 6 carbon atoms, with at least one carbon-carbon double bond; "alkynyl" group is intended to cover both straight- and branched-chain alkyl group having from 2 to 8 carbon atoms, preferably 2 to 6 carbon atoms, with at least one carbon-carbon triple bond.

The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of alkyl alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but not limited to phenyl, naphthyl, biphenyl, anthryl, tetrahydronaphthyl, phenanthryl.

The term "substituted aryl" refers to aryl as just defined having one or more substituents from the group including halogen, CN, OH, $NO_2$, amino, alkyl, cycloalkyl, alkenyl, alkynyl, alkoxy, aryloxy, substituted allyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one or more substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "alkoxy" is used herein to refer to the OR group, where R is alkyl or substituted alkyl. The term "aryloxy" is used herein to refer to the OR group, where R is aryl or substituted aryl. The term "alkylcarbonyl" is used herein to refer to the RCO group, where R is alkyl or substituted alkyl. The term "alkylcarboxy" is used herein to refer to the COOR group, where R is alkyl or substituted alkyl. The term "aminoalkyl" refers to both secondary and tertiary amines wherein the alkyl or substituted alkyl groups may be either same or different and the point of attachment is on the nitrogen atom. The term "thioalkyl" is used herein to refer to the SR group, where R is alkyl or substituted alkyl. The term "halogen" refers to Cl, Br, F, and I element.

The anti-progestin compounds of this invention can be prepared following the Schemes illustrated below:

Cyclocarbamate Derivatives

Processes for Preparing Thiophene Cyclocarbamate Derivatives

A. Methods for synthesizing the thiophene cyclocarbamate compounds depicted in Scheme 1 are described below:

Scheme 1

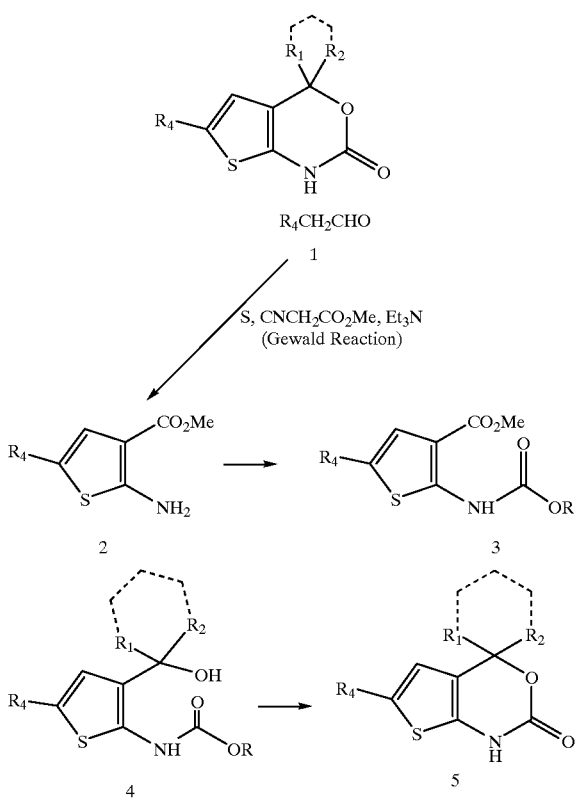

Thus the amino thiophene ester 2 was prepared according to a literature procedure involving the Gewald reaction (see Comprehensive Heterocyclic Chemistry II. A Review of the Literature 1982–1995. A. R. Katritsky et al. Vol. 2 page 639), i.e. the reaction of a suitably substituted aromatic acetaldehyde with sulfur and methyl cyanoacetate in refluxing methanol (Scheme 1). Reaction of the 2-amino group with a suitable chloroformate or carbonate affords the protected amine 3. This can be accomplished by allowing 2 to react with a chloroformate or carbonate derivative such as methyl chloroformate, ethyl chloroformate, allyl chloroformate, 2-(trimethylsilyl)ethyl chloroformate or di-tert-butyldicarbonate in a solvent such as benzene, toluene, xylene, dichloromethane, tetrahydrofuran or pyridine. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Treatment of the protected amino compound 3 with an organo-metallic reagent such as a Grignard reagent, an alkyl or aryl-zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 4. Compound 4 may then be subjected to basic conditions to effect ring closure to give the cyclocarbamate derivative 5. Suitable conditions would involve treatment of 4 with a base such as potassium hydroxide in a solvent such as ethanol or potassium t-butoxide in a solvent such as tetrahydrofuran. The reaction can be carried out in an inert atmosphere (nitrogen or argon) from 0° C. up to the reflux temperature of the solvent.

Scheme 2

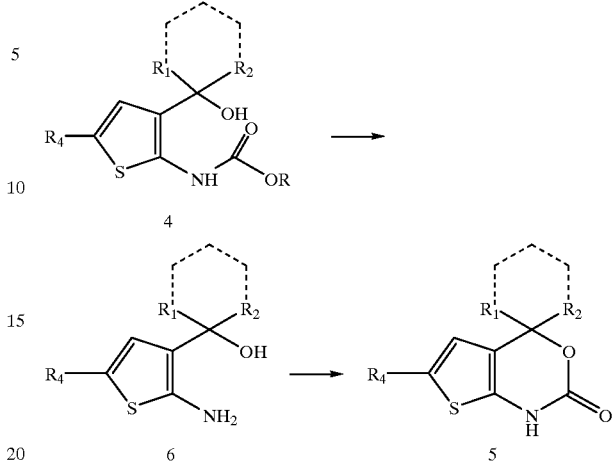

Alternatively the carbamate protecting group present in 4 may be removed under conditions appropriate for its removal to afford 6 (Scheme 2). Subsequent ring closure of 6 with a reagent such as phosgene, carbonyldiimidazole or dimethyl carbonate in an appropriate solvent (tetrahydrofuran, dichloromethane, benzene, etc.) also will provide access to 5.

Scheme 3

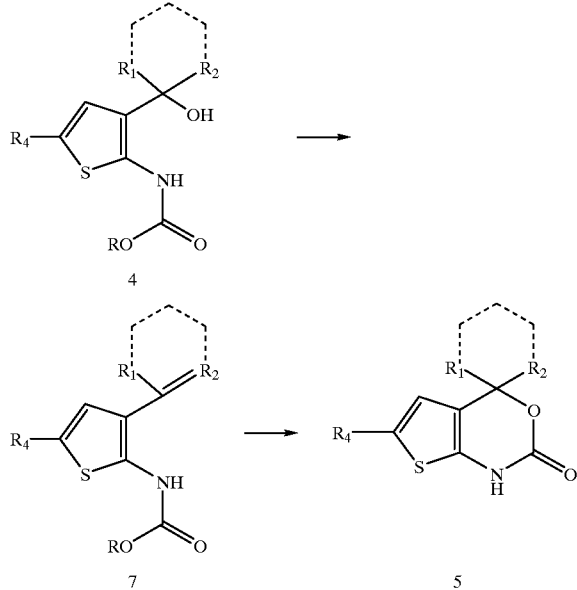

Alternatively, compound 4 may be dehydrated to afford the isopropene derivative 7 (Scheme 3). Suitable conditions for the dehydration would be the use of a reagent such as acetic anhydride, methanesulfonyl chloride, p-toluenesulfonyl chloride or trifluoromethane sulfonyl chloride or anhydride, in a solvent such as pyridine, tetrahydrofuran, dichloromethane or benzene. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Exposure of 7 to acidic conditions would then afford ring closure to give 5. Suitable conditions would be the use of an acid such as p-toluenesulfonic acid, methanesulfonic acid or camphorsulfonic acid in a solvent such as dichloromethane, benzene, toluene or tetrahydrofuran. The reaction can be carried out under an inert atmosphere (nitrogen or argon) from 0° C. up to the reflux temperature of the solvent.

Scheme 4

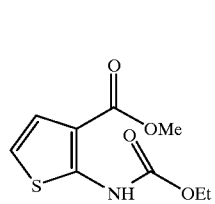

8

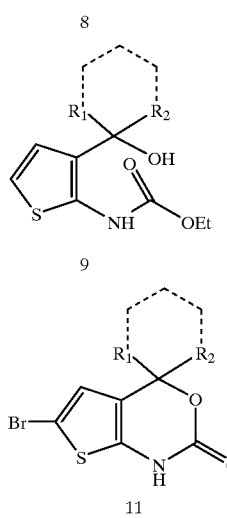

9

10

11

5

An alternative route to 5 is shown in Scheme 4. Treatment of the previously described compound 8 (M. Sugiyama, T. Sakamoto, K. Tabata, K. Endo, K. Ito, M. Kobayashi, H. Fukiumi, *Chem. Pharm. Bull.*, 37(8): 2091 (1989)) with an organo-metallic reagent such as a Grignard reagent, an alkyl or aryl zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 9. Compound 9 may then be subjected to basic conditions to effect ring closure to give the cyclocarbamate derivative 10. Suitable conditions would involve treatment of 10 with a base such as potassium hydroxide in a solvent such as ethanol or potassium t-butoxide in a solvent such as tetrahydrofuran. The reaction can be carried out in an inert atmosphere (nitrogen or argon) from 0° C. up to the reflux temperature of the solvent. Compound 10 may then be converted to the brominated derivative 11. Suitable conditions would be treatment with bromine or N-bromosuccinimide in a solvent such as dichloromethane, tetrahydrofuran or acetic acid. The reaction can be carried out in an inert atmosphere (nitrogen or argon) from 0° C. up to the reflux temperature of the solvent in the presence of an additive such as silica gel. Subsequent reaction of 11 with an aryl or heteroaryl boronic acid, boronic acid anhydride or trialkyl stannane then provides access to the desired biaryl compound 5. The reaction can be carried out in a solvent such as acetone, ethanol, benzene, toluene or tetrahydrofuran, under an inert atmosphere (nitrogen or argon) from 0° C. up to the reflux temperature of the solvent, in the presence of a palladium catalyst such as tetrakis(triphenylphosphine)palladium (0) or palladium acetate and may require an additive such as sodium carbonate, cesium fluoride or potassium phosphate.

Scheme 5

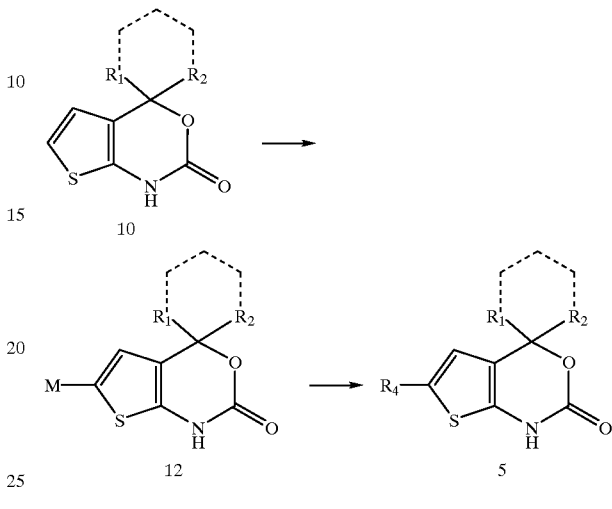

10

12

5

Alternatively, 10 (Scheme 5) may be treated at low temperature with a reagent such as an alkyl lithium or lithium amide in an inert solvent such as tetrahydrofuran, and then converted to a boronic acid 12 (M=B(OH)$_2$) under the action of trimethyl or triisopropyl borate, or into a stannane via reaction with trimethyltin chloride or bis (trimethyltin). Subsequent reaction of 12 with an aryl or heteroaryl bromide or iodide in the presence of a palladium catalyst such as tetrakis(triphenylphosphine)palladium (0) or palladium acetate and may require an additive such as sodium carbonate, cesium fluoride or potassium phosphate, would then effect conversion into the desired thiophene cyclocarbamate 5.

B. Methods for synthesizing the thiophene cyclocarbamate compounds depicted in Scheme 6 are described below:

Scheme 6

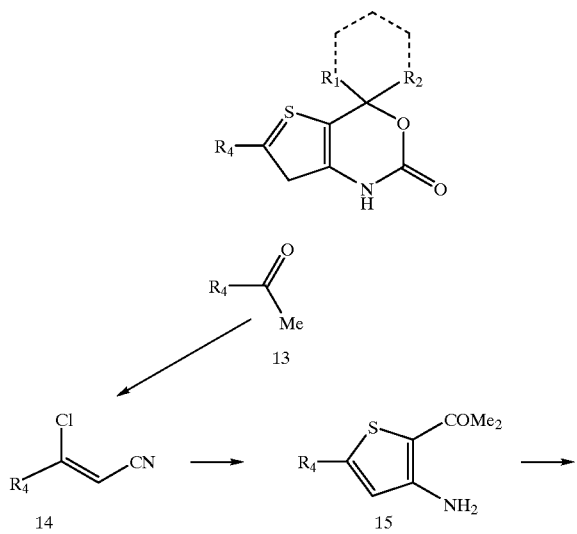

13

14

15

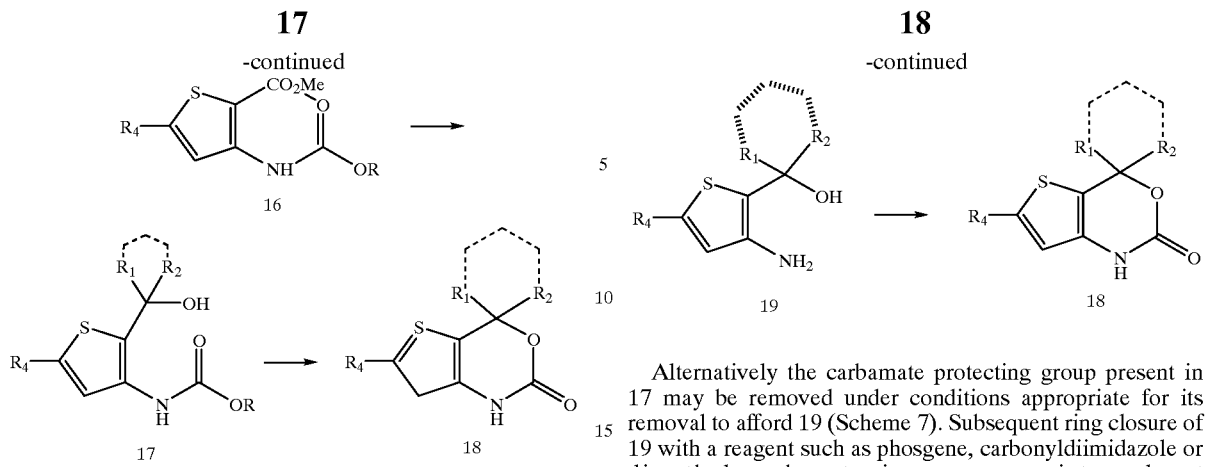

The amino thiophene compounds 15 (Scheme 6) are prepared according to a literature procedure (Comprehensive Heterocyclic Chemistry II. A Review of the Literature 1982–1995. A. R. Katrisky et al., Vol. 2, page 639) which involves treating a suitably substituted aromatic methyl ketone 13 with phosphorus oxychloride in N,N-dimethyl formamide to afford the chloro cyano olefin derivative 14. Allowing 14 to react with methyl mercaptoacetate in methanol containing sodium methoxide affords the key aminothiophene carboxylate starting material. Reaction of the 2-amino group with a suitable chloroformate or carbonate affords the protected amine 16. This can be accomplished by allowing 15 to react with a chloroformate or carbonate derivative such as methyl chloroformate, ethyl chloroformate, allyl chloroformate, 2-(trimethylsilyl)ethyl chloroformate or di-tert-butyldicarbonate in a solvent such as benzene, toluene, xylene, dichloromethane, tetrahydrofuran or pyridine. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Treatment of the protected amino compound 16 with an organometallic reagent such as a Grignard reagent, an alkyl or aryl-zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 17. Compound 17 may then be subjected to basic conditions to effect ring closure to give the cyclocarbamate derivative 18. Suitable conditions would involve treatment of 4 with a base such as potassium hydroxide in a solvent such as ethanol or potassium t-butoxide in tetrahydrofuran. The reaction can be carried out in an inert atmosphere (nitrogen or argon) from 0° C. up to the reflux temperature of the solvent.

Scheme 7

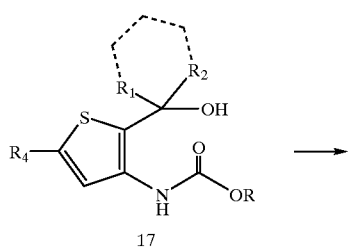

Alternatively the carbamate protecting group present in 17 may be removed under conditions appropriate for its removal to afford 19 (Scheme 7). Subsequent ring closure of 19 with a reagent such as phosgene, carbonyldiimidazole or dimethyl carbonate in an appropriate solvent (tetrahydrofuran, dichloromethane, benzene, etc.) also will provide access to 18.

Scheme 8

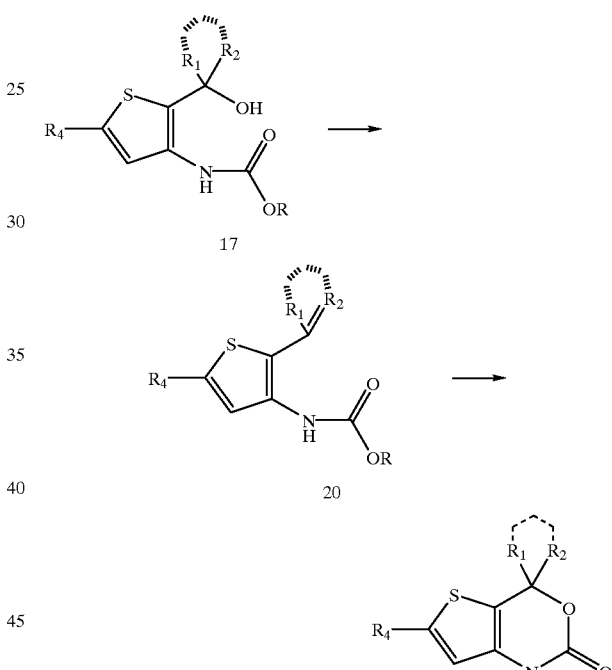

Alternatively, compound 17 may be dehydrated to afford the isopropene derivative 20 (Scheme 8). Suitable conditions for the dehydration would be the use of a reagent such as acetic anhydride, methanesulfonyl chloride, p-toluenesulfonyl chloride or trifluoromethane sulfonyl chloride or anhydride, in a solvent such as pyridine, tetrahydrofuran, dichloromethane or benzene. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Exposure of 20 to acidic conditions would then afford ring closure to give 18. Suitable conditions would be the use of an acid such as p-toluenesulfonic acid, methanesulfonic acid or camphorsulfonic acid in a solvent such as dichloromethane, benzene, toluene or tetrahydrofuran. The reaction can be carried out under an inert atmosphere (nitrogen or argon) from 0° C. up to the reflux temperature of the solvent.

Scheme 9

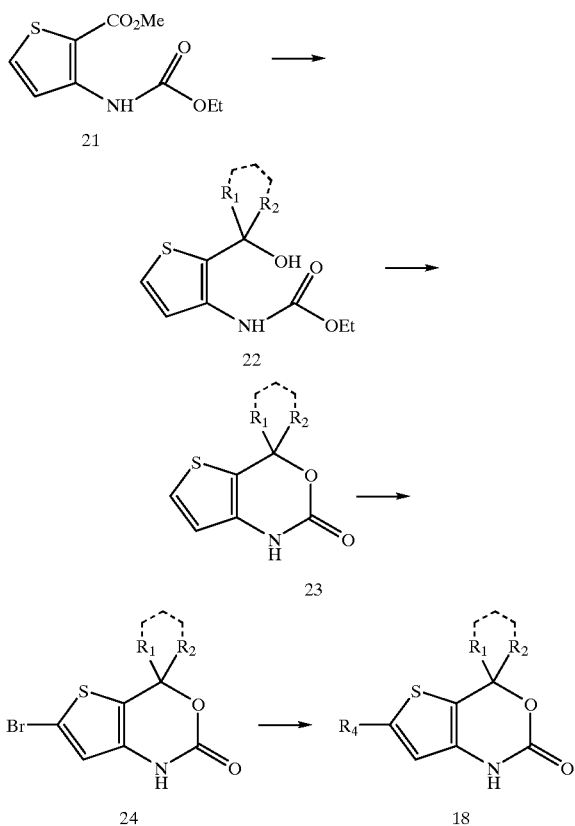

An alternative route to 18 is shown in Scheme 9. Treatment of the previously described compound 21, as taught by H. Fukiumi, M. Sugiyama, T. Sakamoto, *Chem. Pharm. Bull.*, 37(5):1197 (1989), with an organo-metallic reagent such as a Grignard reagent, an alkyl or aryl zinc reagent, an alkyl or aryl lithium reagent in an inert solvent (tetrahydrofuran, diethylether) under an inert atmosphere (nitrogen or argon) at a suitable temperature from 0° C. up to reflux temperature of the solvent will then provide the tertiary alcohol 22. Compound 22 may then be subjected to basic conditions to effect ring closure to give the cyclocarbamate derivative 23. Suitable conditions would involve treatment of 22 with a base such as potassium hydroxide in a solvent such as ethanol or potassium t-butoxide in tetrahydrofuran The reaction can be carried out in an inert atmosphere (nitrogen or argon) from 0° C. up to the reflux temperature of the solvent. Compound 23 may then be converted to the brominated derivative 24. Suitable conditions would be treatment with bromine or N-bromosuccinimide in a solvent such as dichloromethane, tetrahydrofuran or acetic acid. The reaction can be carried out in an inert atmosphere (nitrogen or argon) from 0° C. up to the reflux temperature of the solvent in the presence of an additive such as silica gel. Subsequent reaction of 24 with an aryl or heteroaryl boronic acid boronic acid anhydride or trialkyl stannane then provides access to the desired biaryl compound 18. The reaction can be carried out in a solvent such as acetone, ethanol, benzene, toluene or tetrahydrofuran, under an inert atmosphere (nitrogen or argon) from 0° C. up to the reflux temperature of the solvent, in the presence of a palladium catalyst such as tetrakis (triphenylphosphine)palladium (0) or palladium acetate and may require an additive such as sodium carbonate, cesium fluoride or potassium phosphate.

Scheme 10

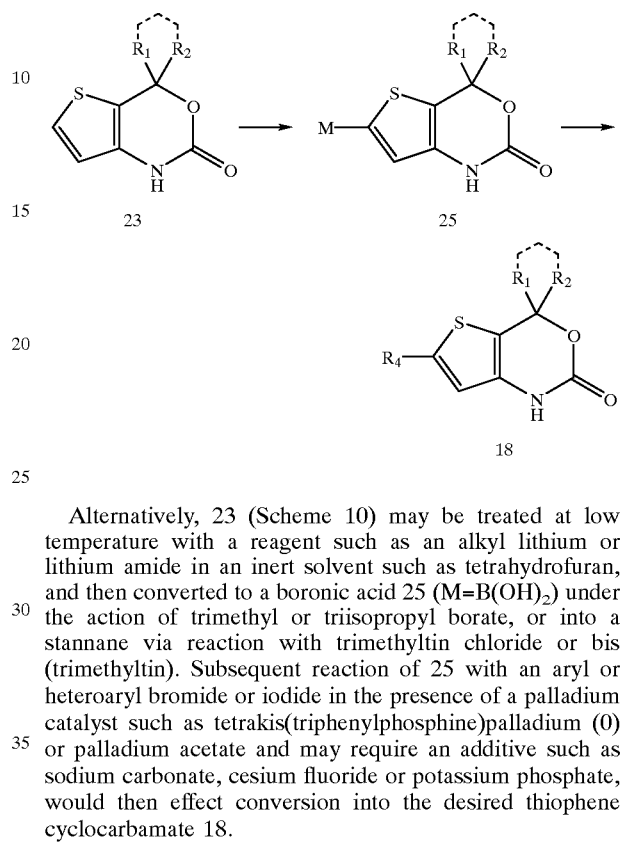

Alternatively, 23 (Scheme 10) may be treated at low temperature with a reagent such as an alkyl lithium or lithium amide in an inert solvent such as tetrahydrofuran, and then converted to a boronic acid 25 (M=B(OH)$_2$) under the action of trimethyl or triisopropyl borate, or into a stannane via reaction with trimethyltin chloride or bis (trimethyltin). Subsequent reaction of 25 with an aryl or heteroaryl bromide or iodide in the presence of a palladium catalyst such as tetrakis(triphenylphosphine)palladium (0) or palladium acetate and may require an additive such as sodium carbonate, cesium fluoride or potassium phosphate, would then effect conversion into the desired thiophene cyclocarbamate 18.

C. Method for synthesizing the thiophene thiocyclocarbamate compounds 26 and 27 depicted in Scheme 11 are described below:

Scheme 11

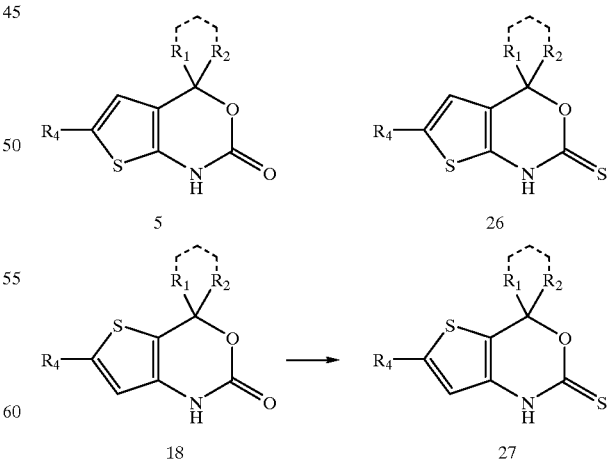

Thiophene thiocyclocarbamates 26 and 27 may be obtained directly by treating 5 and 18 respectively with phosphorus pentasulfide in refluxing pyridine. Alternatively 5 and 18 may be treated with Lawesson's reagent ([2,4-bis(4- methoxyphenyl)-1,3-dithia-2,4-diphosphetane-2,4-disulfide]) in refluxing pyridine to afford 26 and 27, respectively.

Process for Making Thiazole Cyclocarbamate Derivatives

Methods for preparing the thiazole cyclocarbamate compounds are described below.

Scheme 12

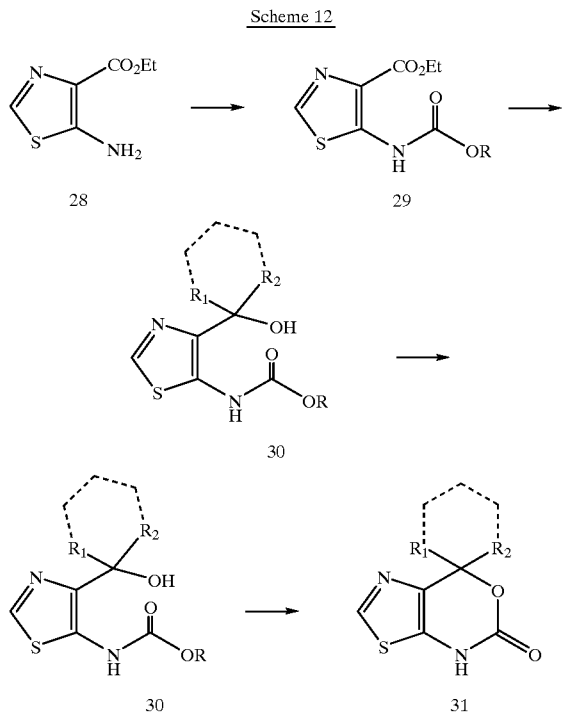

Thus the thiazole 28 was prepared according to a literature procedure, scheme 12 by B. Golankiewicz and P. Januszczyk, *Tetrahedron*, 41:5989 (1985). Reaction of the amine 28 with a suitable chloroformate or carbonate then gives the protected amine 29. This may be accomplished by reacting compound 28 with a chloroformate or carbonate derivative such as methylchloroformate, ethylchloroformate, allylchloroformate, 2-(trimethylsilyl) ethylchloroformate or di-tert-butyldicarbonate in a solvent such as dichloromethane, THF, benzene, xylene or pyridine. The reaction can be carried out under an inert atmosphere (nitrogen or argon) from 0 ° C. up to the reflux temperature of the solvent and may require the presence of a base such as 4-dimethylaminopyridine, triethylamine, pyridine or di-isopropyl ethylamine. Exposure of compound 29 to an organo-metallic reagent such as a Grignard reagent, an alkyl or aryl-zinc reagent, an alkyl or aryl lithium reagent in an inert solvent (THF, diethyl ether) under an inert atmosphere (nitrogen or argon) at a suitable temperature from 0° C. up to the reflux temperature of the solvent will then provide the alcohol 30. Compound 30 may then be exposed to basic conditions to effect ring closure to give the cyclocarbamate derivative 31. Suitable conditions would involve treatment of compound 30 with a base such as potassium hydroxide in a solvent such as ethanol. The reaction can be carried out under an inert atmosphere (nitrogen or argon) from 0° C. up to the reflux temperature of the solvent.

Scheme 13

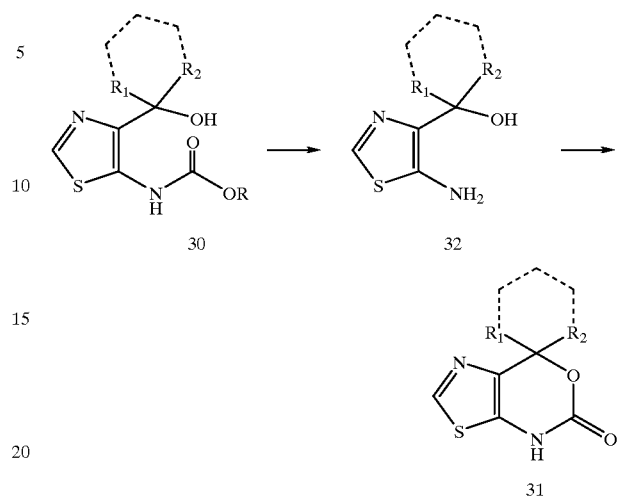

Alternatively the carbamate protecting group present in compound 30 may be removed under conditions appropriate for its removal to afford compound 32 as taught by T. W. Greene and P. G. M. Wuts, Protective Groups in Organic Synthesis, second ed., Wiley-Interscience (1991). Subsequent ring closure of compound 32 with a reagent such as phosgene, carbonyl diimidazole or dimethyl carbonate in an appropriate solvent (THF, dichloromethane, benzene, etc) will also provide access to compound 31.

Scheme 14

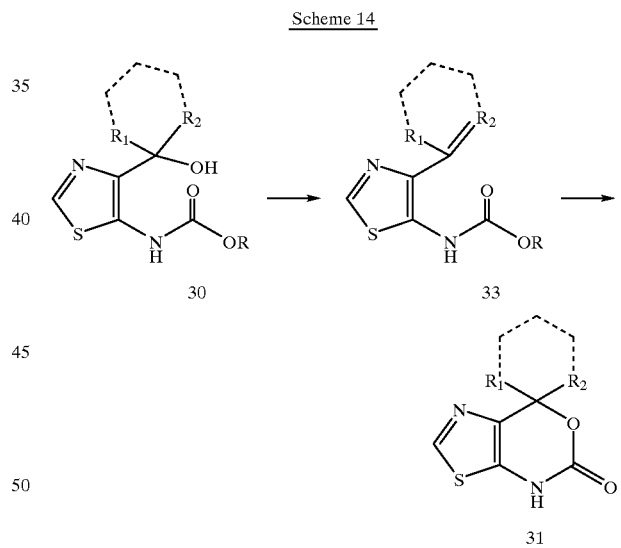

Alternatively, if compound 30 is a tertiary alcohol then it may be dehydrated to afford the isopropene derivative 33, scheme 3. Suitable conditions for the dehydration would the use of a reagent such as acetic anhydride, methanesulfonyl chloride, p-toluenesulfonyl chloride or trifluoromethane sulfonyl chloride or anhydride, in a solvent such as pyridine, THF, dichloromethane or benzene. The reaction can be carried out under an inert atmosphere (nitrogen or argon) from 0° C. up to the reflux temperature of the solvent and may require the presence of a base such as 4-dimethylaminopyridine, triethylamine, pyridine or di-isopropyl ethylamine. Exposure of compound 33 to acidic conditions would then afford ring closure to give compound 31. Suitable conditions would be the use of an acid such as p-toluenesulfonic acid, methanesulfonic acid or camphorsulfonic acid in a solvent such as dichloromethane, benzene, toluene or THF and the reaction can be carried out under an inert atmosphere (nitrogen or argon) from 0° C. up to the reflux temperature of the solvent.

Scheme 15

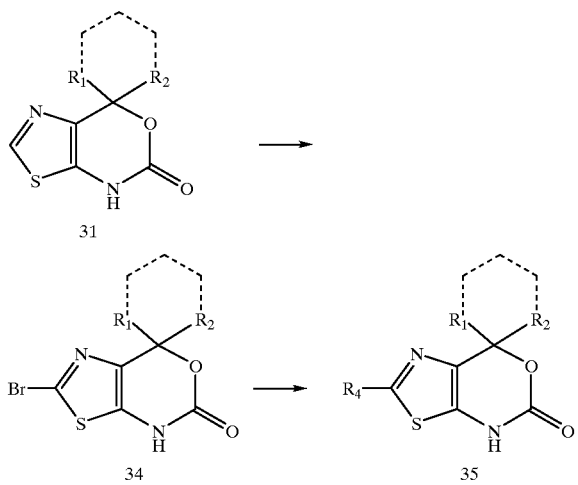

Compound 31 may then be converted into the bromide 34, scheme 15. Suitable conditions would be exposure to bromine or N-bromosuccinimide in a solvent such as dichloromethane, THF or acetic acid, the reaction can be carried out under an inert atmosphere (nitrogen or argon) from 0° C. up to the reflux temperature of the solvent in the presence of an additive such as silica gel. Subsequent reaction of compound 34 with an aryl or heteroaryl boronic acid, boronic acid anhydride or trialkyl stannane then provides access to the desired biaryl compound 35. The reaction can be carried out in a solvent such as acetone, ethanol, benzene, toluene or THF, under an inert atmosphere (nitrogen or argon) from 0° C. up to the reflux temperature of the solvent, in the presence of a palladium catalyst such as tetrakis(triphenylphosphine)palladium (0) or palladium acetate and may require an additive such as sodium carbonate, cesium fluoride or potassium phosphate.

Scheme 16

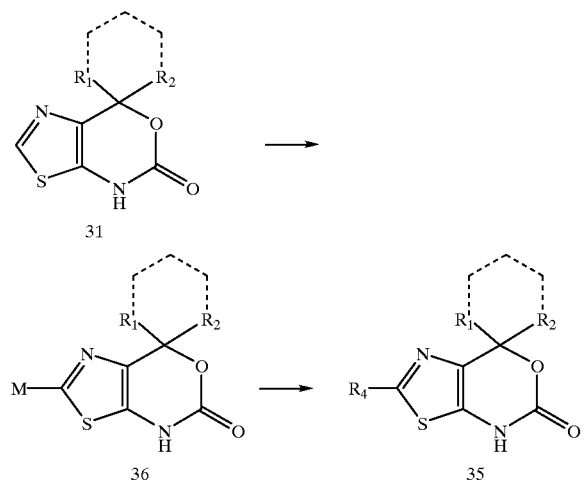

Alternatively compound 31 may be treated at low temperature with a reagent such as an alkyl lithium or lithium amide in an inert solvent such as THF, and then converted into a boronic acid ($M=B(OH)_2$) 36 under the action of trimethyl or triisopropyl borate, or into a stannane under the action of trimethyltin chloride or bis(trimethyltin), Scheme 16. Subsequent reaction with an aryl or heteroaryl bromide or iodide in the presence of a palladium catalyst such as tetrakis(triphenylphosphine)palladium (0) or palladium acetate and may require an additive such as sodium carbonate, cesium fluoride or potassium phosphate would then effect conversion into the desired compound 35.

Amide Derivatives
Process for Making Amide Thiophene Derivatives
A method for preparing thiophene derivatives is described below, scheme 17.

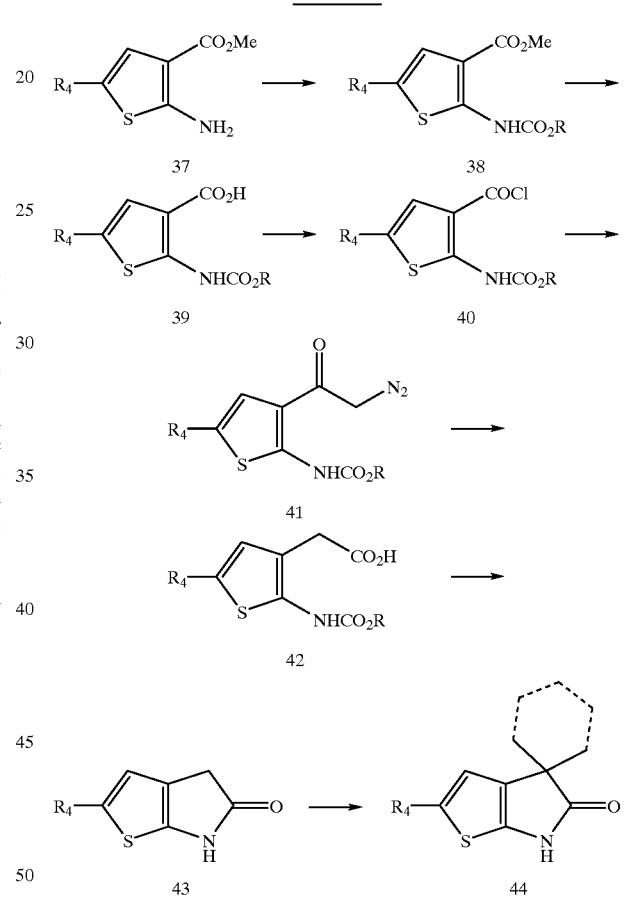

Thus the amine 37 is converted into a carbamate, such as a tert-butyl carbamate as described in scheme 1 for the preparation of compound 2. Hydrolysis of the ester 38 under basic conditions, for example lithium or sodium hydroxide in THF or methanol at room temperature then gives the acid 39. Conversion of the acid 39 into the acid chloride 40 is accomplished under standard conditions, thionyl chloride or oxalyl chloride either neat or in the presence of a solvent such as dichloromethane and an additive such as a catalytic amount of N,N-dimethylformamide. Compound 40 is then reacted with diazomethane or trimethylsilyldiazomethane in an inert solvent such as THF or dichloromethane, and the product diazoketone 41 is then rearranged in the presence of silver (I) oxide to afford the acid 42. Treatment of compound 42 under conditions that specifically remove the protecting carbamate functionality, for example acidic conditions, will then affect cyclization to give compound 43. Reaction of compound 43 with an alkylating agent such as an alkyl iodide, bromide, tosylate or mesylate, or a bis-alkyl iodide, bromide, tosylate or mesylate, under basic conditions, for example butyl lithium in the presence of N,N,N,N-tetramethylene diamine in a solvent such as THF under an inert atmosphere (nitrogen or argon) at a temperature between −78° C. and the boiling point of the solvent, will then afford the alkylated derivative 44.

Process for Making Thiazole Derivatives

A method for preparing thiazole derivatives is described below, scheme 18.

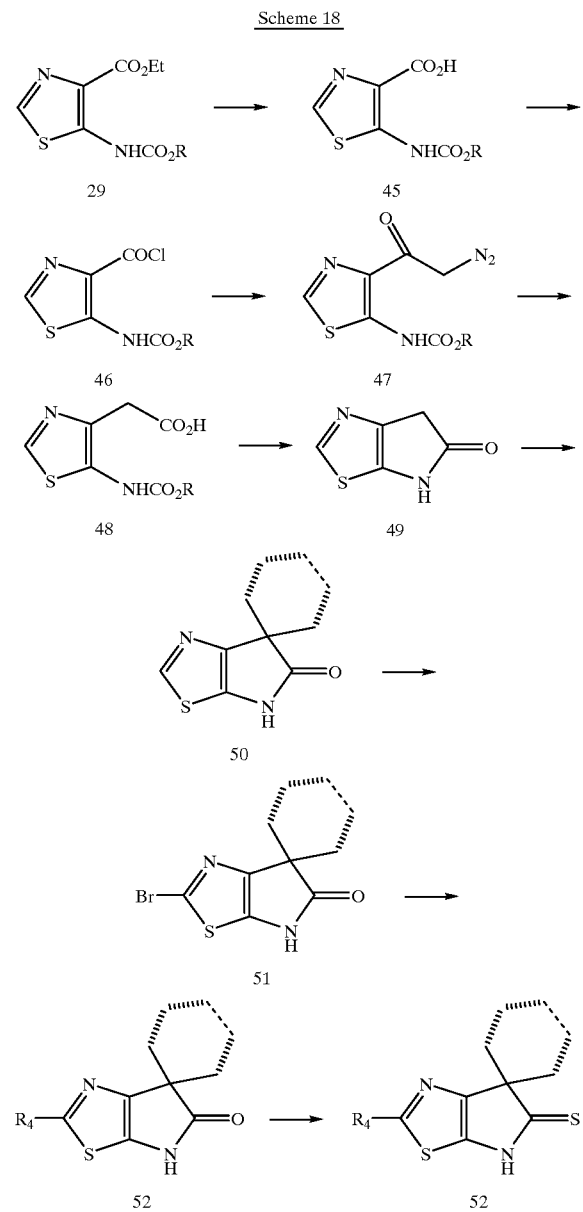

Scheme 18

Hydrolysis of the ester 29 under basic conditions, for example lithium or sodium hydroxide in THF or methanol at room temperature then gives the acid 45. Conversion of the acid 45 into the acid chloride 46 is accomplished under standard conditions, for example thionyl chloride or oxalyl chloride either neat or in the presence of a solvent such as dichloromethane and an additive such as a catalytic amount of N,N-dimethylformamide. Compound 46 is then reacted with diazomethane or trimethylsilyldiazomethane in an inert solvent such as THF or dichloromethane, and the product diazoketone 47 is then rearranged in the presence of silver (I) oxide to afford the acid 48. Treatment of compound 48 under conditions that specifically remove the protecting carbamate functionality, for example acidic conditions, will then affect cyclization to give the heterocycle 49. Reaction of compound 49 with an alkylating agent such as an alkyl iodide, bromide, tosylate or mesylate, or a bis-alkyl iodide, bromide, tosylate or mesylate, under basic conditions, for example butyl lithium in the presence of N,N,N,N-tetramethylene diamine in a solvent such as THF under an inert atmosphere (nitrogen or argon) at a temperature between −78° C. and the boiling point of the solvent, will then afford the alkylated heterocycle 50. Compound 50 may then be converted into the bromide 51. Suitable conditions would be exposure to bromine or N-bromosuccinimide in a solvent such as dichloromethane, TMF or acetic acid, the reaction can be carried out under an inert atmosphere (nitrogen or argon) from 0° C. up to the reflux temperature of the solvent in the presence of an additive such as silica gel. Subsequent reaction of compound 51 with an aryl or heteroaryl boronic acid, boronic acid anhydride or trialkyl stannane then provides access to the desired biaryl compound 52. The reaction can be carried out in a solvent such as acetone, ethanol, benzene, toluene or THF, under an inert atmosphere (nitrogen or argon) from 0° C. up to the reflux temperature of the solvent, in the presence of a palladium catalyst such as tetrakis(triphenylphosphine)palladium (0) or palladium acetate and may require an additive such as sodium carbonate, cesium fluoride or potassium phosphate. The thione derivative, compound 53, may be obtained directly by treating 52 with phosphorus pentasulfide in refluxing pyridine. Alternatively 52 may be treated with Lawesson's reagent in refluxing pyridine to afford 53.

The anti-progestin compounds of the formulations of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

These methods of treatment may be used for contraception or for the treatment and/or prevention of secondary amenorrhea, dysfunctional bleeding, uterine leiomyomata, endometriosis; polycystic ovary syndrome, carcinomas and adenocarcinomas of the endometrium, ovary, breast, colon, prostate, or minimization of side effects or cyclic menstrual bleeding. Additional uses of the invention include stimulation of food intake.

When the combined compounds are employed for the utilities described above, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof and vegetable oil.

The following non-limiting examples are illustrative of exemplary compound 5.

EXAMPLE 1

6-(3-chlorophenyl)-1,4-dihydro-4,4-dimethyl-2H-thieno[2,3-d][1,3]oxazine-2-one 2-(3-Chlorobenzyl)acetaldehyde To a 25° C. solution of 3-chlorostyrene in anhydrous $CH_2Cl_2$ (10.0 g, 72.15 mmol) was added a well-stirred solution of $Pb(OAc)_4$ (35.2 g, 79.4 mmol) in trifluoroacetic acid (150 mL), dropwise. Reaction was completed within 30 minutes of the addition and after being stirred for a further 30 minutes, the mixture was poured into water, extracted with ether (3×), the combined organic layers were washed with saturated $NaHCO_3$ solution, water, dried ($MgSO_4$), and concentrated to a volume of about 15 mL and immediately used for the following reaction described below.

2-Amino-5-(3-chloro-phenyl)-thiophene-3-carboxylic acid methyl ester

To the crude aldehyde, prepared above, in methanol was added a mixture of sulfur (2.55 g, 79.44 mmol), methylcyanoacetate (7.88 g, 79.44 mmol), morpholine (6.92 g, 79.44) and the resulting reaction mixture was refluxed for 16 hours. The unreacted sulfur was filtered off and the filtrates were evaporated leaving behind a black residue. This residue was extracted with ether, washed with $H_2O$. Crystallized from ether/hexane (1:5) to obtain white crystals (3.85 g, 14.3 mmol, 50%), mp 85–87°;
$^1$H NMR (DMSO-$d_6$) δ3.75 (s, 3H), 7.18–7.27 (m, 1H), 7.31–7.42 (m, 3H), 7.53 (s, 1H), 7.62 (s, 1H); MS(+APCI) m/z268(M+H); Anal. Calc. For $C_{12}H_{10}ClNO_2S$: C, 53.83, H, 3.76, N, 5.23. Found: C, 53.57; H, 3.37; N, 5.00.

2-Allyloxycarbonylamino-5-(3-chloro-phenyl)-thiophene-3-carboxylic acid methyl ester To a solution of 2-amino-5-(3-chloro-phenyl)-thiophene-3-carboxylic acid methyl ester (2 g, 7.5 mmol) in anhydrous 1,2-dichloroethane (50 mL) was added at room temperature under nitrogen alkyl chloroformate (1.6 mL, 15.1 mmol). The reaction mixture was heated at reflux under nitrogen for 18 hours, cooled to room temperature, and treated with a saturated aqueous sodium bicarbonate solution (100 mL). The organic layer was separated and aqueous layer was extracted with methylene chloride (3×20 mL). The combined organic layers were washed (brine) and dried ($MgSO_4$). After removal of the solvent, the residue was purified by a flash silica gel column (hexane:ethyl acetate/7:1) to give the subtitled compound as an off-white solid (2.14 g, 81%): $^1$H-NMR (DMSO-$d_6$) δ10.2 (s, 1H), 7.73 (t, 1H, J=1.7 Hz), 7.66 (s, 1H), 7.57 (dt, 1H, J=7.7, 1.7 Hz), 7.41 (t, 1H, J=7.7 Hz), 7.34 (dt, 1H, J=6.8, 1.6 Hz), 6.01 (m, 1H), 5.41 (dd, 1H, J=7.3, 1.6 Hz), 5.29 (dd, 1H, J=10.5, 1.3 Hz), 4.74 (d, 2H, J=5.5 Hz), 3.84 (s, 3H). Anal. Calc. For $C_{16}H_{14}ClNO_4S$: C, 54.63; H, 4.01; N, 3.98. Found: C, 54.56; H, 3.92; N, 3.89.

To a solution of 2-allenoxycarbonylamino-5-(3-chloro-phenyl)-thiophene-3-carboxylic acid methyl ester (0.1 g, 0.28 mmol) in anhydrous THF was added a solution of methylmagnesium bromide (3.0 M in diethyl ether, 1.5 mL, 4.5 mmol) at room temperature under nitrogen. After stirring at room temperature under nitrogen for 20 minutes, the reaction mixture was treated with brine (10 mL) followed by addition of an aqueous 1N HCl solution (5 mL). Ethyl acetate (20 mL) was added and organic layer was separated, washed with brine (5 mL) and dried over $MgSO_4$. After removal of solvent, the residue was purified by a flash column (silica gel, hexane:ethyl acetate/5:1) to give carbinol which was used in next step without further purification and characterization.

A mixture of above crude carbinol, potassium hydroxide (excess) in ethanol was stirred at room temperature under nitrogen overnight. The reaction solution was then acidified by an addition of a cold aqueous 1N HCl solution. Ethyl acetate (20 mL) was added and organic layer was separated, washed with brine (5 mL) and dried ($MgSO_4$). After removal of the solvent, the residue was purified by a silica gel column (hexane:ethyl acetate/2:1) to give the title compound as an off-white solid (16 mg, 19% for two steps): mp 149–150° C.; $^1$H-NMR (DMSO-$d_6$) δ10.69 (s, 1H), 7.64 (t, 1H, J=1.8 Hz), 7.49 (s, 1H), 7.47 (dt, 1H, J=7.7, 1.4 Hz), 7.39 (t, 1H, J=7.8 Hz), 7.29 (dt, 1H, J=7.8, 1.3 Hz), 1.61 (s, 6H). MS (EI) m/z 293/295 (M$^+$). Anal. Calc. For $C_{14}H_{12}ClNO_2S$: C, 57.24; H, 4.12; N, 4.77. Found: C, 57.27; H, 4.25; N, 4.66.

EXAMPLE 2

6-(3-chlorophenyl)-1,4-dihydro-4,4-dimethyl-2H-thieno[3,2-d][1,3]oxazine-2-one

3-Chloro-3-(3-chlor-phenyl)-acrylonitrile

A solution of $POCl_3$ was slowly added to anhydrous DMF over a period of 20 minutes and the temperature was maintained around 30° C. 3'-Chloroacetophenone solution in anhydrous DMF was added to the above solution and the reaction temperature was allowed to rise to around 50° C. Hydroxylamine HCl was added to the reaction solution, portionwise, over 1 hour. A volume of 500 mL of water was added to form precipitate, stirred for 1 hour and the precipitate was collected on a Buchner funnel, washed with $H_2O$, and dried to afford a yellow crystalline compound, mp 60–62° C. $^1H$ NMR (DMSO-$d_6$) δ1.60 (s, 6H), 7.30 (d, 1H, J=8.41 Hz), 7.41 (d, 1H, J=8.41 Hz), 10.47 (s, 1H); MS(+APCI)m/z 213(M+H); Anal. Calc. For $C_9H_9ClN_2O_2$: C, 50.84; H, 4.27; N, 13.17. Found: C, 50.99; H, 4.28; N, 12.98.

3-Amino-5-(3-chloro-phenyl)-thiophene-2-carboxylic acid methyl ester

Sodium pellets were slowly added to methanol solution to form NaOMe in situ, then methyl thioglycolate was added over a period of 20 minutes to the methanol solution. A solution of 3-Chloro-3-(3-chloro-phenyl)-acrylonitrile in methanol was added slowly and was brought to reflux for 1 hour. The reaction mixture was cooled to room temperature and methanol was concentrated to 100 mL and 200 mL of water was added, stirred for 30 min and the yellow precipitate was collected and washed with water several times to yield a yellow crystalline compound, mp 92–95° C. $^1H$ NMR (DMSO-$d_6$) δ1.60 (s, 6H), 7.30 (d, 1H, J=8.41 Hz), 7.41 (d, 1H, J=8.41 Hz), 10.47 (s, 1H); MS (+APCI) m/z 213(M+H); Anal. Calc. For $C_9H_9ClN_2O_2$: C, 50.84; H, 4.27; N, 13.17. Found: C, 50.99; H, 4.28; N, 12.98.

3-Allyloxycarbonylamino-5-(3-chloro-phenyl)-thiophene-2-carboxylic acid methyl ester To a solution of 3-Amino-5-(3-chloro-phenyl)-thiophene-2-carboxylic acid methyl ester (15 g, 56.0 mmol) in toluene (200 mL) was added a solution of alkyl chloroformate (8.10 g, 67.2 mmol) in toluene (5.0 mL) and the resulting reaction solution was heated under reflux for 3 hours. Toluene was stripped down and the crystals were collected and washed with etherihexane to afford a yellow crystalline compound, mp 101"103° C. $^1H$ NMR (DMSO-$d_6$) δ3.85 (s, 3H), 4.68"4.71 (d, 2H, J=5.46 Hz), 5.26–5.30 (dd, 1H, J=1.35, 9.84 Hz), 5.36–5.42 (dd, 1H, J=1.57, 15.68 Hz), 5.96 (m, 2H), 7.50–7.52 (m, 2H), 7.67–7.71 (m, 1H), 7.79 (s, 1H), 8.10 (s, 1H); MS(+APCI) m/z 352(M+H); Anal. Calc. For $C_{16}H_{14}ClNO_4S$: C, 54.63; H, 4.01; N, 3.97. Found: C, 54.05; H, 4.17; N, 3.84.

[5-(3-Chloro-phenyl)-2-(1-hydroxy-1-methyl-ethyl-thiophen-3-yl]-carbamic acid alkyl ester To a solution of 3-Allyloxycarbonylamino-5-(3-chloro-phenyl)-thiophene-2-carboxylic acid methyl ester (5.3 g, 15.1 mmol) in anhydrous THF (30 mL) at room temperature was added a solution of 3.0M MeMgI in ether (20.1 mL, 60.24 mmol). After 30 minutes, the reaction was slowly quenched with $H_2O$ (10 mL), treated with saturated $NH_4OH$ (100 mL), extracted with ether (200 mL), washed with brine, dried ($MgSO_4$), concentrated, and chromatographed (hexane/ether, 1:4): mp 60–61; $^1H$ NMR (DMSO-$d_6$) δ1.52 (s, 6H), 4.59–4.61 (d, 2H, J=5.35 Hz), 5.22–5.36 (m, 2H), 5.91–6.04 (m, 2H), 7.33–7.67 (m, 5H), 8.89 (s, 1H); MS(EI) m/z 351/353(M+H); Anal. Calc. For $C_{17}H_{18}ClNO_3S$: C, 58.03; H, 5.16; N, 3.98. Found: C, 58.17; H, 5.16; N, 3.97.

6-(3-Chlorophenyl)-1,4-dihydro-4,4-dimethyl-2H-thieno[3,2-d][1,3]oxazin-2-one

To a solution of [5-(3-Chloro-phenyl)-2-(1-hydroxy-1-methyl-ethyl)-thiophen-3-yl]-carbanic acid alkyl ester (0.12 g, 0.34 mmol) in anhydrous THF (5.0 mL) was added KO$^t$BU (0.076 g, 0.068 mmol) and stirred for 15 min, quenched with $H_2O$, and in situ crystallization was carried out by adding minimal amount of MeOH to the solution. The white crystals were collected on a Büchner funnel, mp 123–125° C. $^1H$ NMR (DMSO-$d_6$) δ1.64 (s, 6H), 7.05 (s, 1H), 7.37–7.48 (m, 2H), 7.53–7.56 (s, 1H), 7.67–7.68 (m, 1H), 10.41 (s, 1H); MS(EI) m/z 293/295(M+H); Anal. Calc. For $C_{17}H_{18}ClNO_3S$: C, 57.24; H, 4.12; N, 4.77. Found: C, 56.93; H, 3.92; N, 4.97.

EXAMPLE 3

Pharmacology

The progestational activity of the current invention was evaluated in the PRE-luciferase assay in CV-1 cells, described below. In-vitro potencies can be in the range 0.01 nM–10,000 nM. In vivo potencies are anticipated to be in the range 1 mg/kg to 30 mg/kg.

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium: The Growth Medium was as Follows

DMEM (BioWhittaker) containing 10% (v/v) fetal bovine serum (keat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (BioWhittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell Culture, Transfection, Treatment, and Luciferase Assay

Stock CV-1 cells are maintained in growth medium Co-transfection is done using $1.2 \times 10^7$ cells, 5 mg pLEM plasmid with hPR-B inserted at SphI and BaHI sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results

Each treatment consists of at least 4 replicates. Log transformed data are used for analysis of variance and nonlinear dose response curve fitting for both agonist and antagonist modes. Huber weighting is used to downweight the effects of outliners. $EC_{50}$ or $IC_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in full dose-response curves and the EC$_{50}$ or IC$_{50}$ values are calculated.

TABLE 1

Estimated EC$_{50}$, standard error (SE), and 95% confidence intervals (CI) for reference progestins from three individual studies

| Compound | Exp. | EC50 (nM) | SE | 95% CI lower | upper |
|---|---|---|---|---|---|
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 2

Estimated IC$_{50}$, standard error (SE), and 95% confident interval (CI) for the antiprogestin, RU486 from three individual studies

| Compound | Exp. | IC 50 (nM) | SE | 95% CI lower | upper |
|---|---|---|---|---|---|
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

EC$_{50}$: Concentration of a compound that gives half maximal increase PRE-luciferase activity (default-nM) with SE.

IC$_{50}$: Concentration of a compound that gives half-maximal decrease in 3 nM progesterone induced PRE-luciferase activity (default-nM) with SE.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method of contraception which comprises administering to a female of child bearing age for 28 consecutive days:

a) a first phase of from 14 to 24 daily dosage units of a progestational agent equal in progestational activity to about 35 to about 100 μg levonorgestrel;

b) a second phase of from 1 to 11 daily dosage units, at a daily dosage of from about 2 to 50 mg, of an antiprogestin compound of Formula 1:

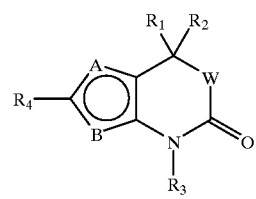

wherein:
A and B are independent substituents selected from the group consisting of S, CH and N;
wherein:
  i) when A is S, B is CH or N;
  ii) when B is S, A is CH or N;
  iii) A and B cannot both be CH; and
  iv) when A and B both equal N, one N may be optionally substituted with an C$_1$ to C$_6$ alkyl group;
R$_1$ and R$_2$ are independent substituents selected from the group consisting of H, C$_1$ to C$_6$ alkyl, substituted C$_1$ to C$_6$ alkyl, C$_2$ to C$_6$ alkenyl, substituted C$_2$ to C$_6$ alkenyl, C$_2$ to C$_6$ alkynyl, substituted C$_2$ to C$_6$ alkynyl, C$_3$ to C$_8$ cycloalkyl, substituted C$_3$ to C$_8$ cycloalkyl, aryl, substituted aryl, heterocyclic, substituted heterocyclic, COR$^A$, and NR$^B$COR$^A$;
or R$_1$ and R$_2$ are fused to form:
  v) an optionally substituted carbon-based, saturated 3 to 8 membered spirocyclic ring;
  vi) an optionally substituted carbon-based 3 to 8 membered spirocyclic ring having one or more carbon-carbon double bonds; or
  vii) an optionally substituted 3 to 8 membered spirocyclic, heterocyclic ring containing in the backbone one to three heteroatoms selected from the group consisting of O, S and N;
R$^A$ is H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;
R$^B$ is H, C$_1$ to C$_3$ alkyl, or substituted C$_1$ to C$_3$ alkyl;
R$^3$ is H, OH, NH$_2$, C$_1$ to C$_6$ alkyl, substituted C$_1$ to C$_6$ alkyl, C$_3$ to C$_6$ alkenyl, substituted C$_1$ to C$_6$ alkenyl, alkynyl, substituted alkynyl, or COR$^C$;
R$^C$ is H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;
R$^4$ is viii) or ix):
  viii) a substituted benzene ring containing the substituents X, Y and Z as shown below,

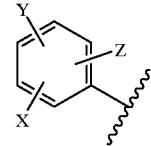

X is selected from the group consisting of halogen, CN, C$_1$ to C$_3$ alkyl, substituted C$_1$ to C$_3$ alkyl, C$_1$ to C$_3$ alkoxy, substituted C$_1$ to C$_3$ alkoxy, C$_1$ to C$_3$ thioalkyl, substituted C$_1$ to C$_3$ thioalkyl, C$_1$ to C$_3$ aminoalkyl, substituted C$_1$ to C$_3$ aminoalkyl, NO$_2$, C$_1$ to C$_3$ perfluoroalkyl, 5 or 6 membered heterocyclic ring containing in its backbone 1 to 3 heteroatoms, $COR^D$, $OCOR^D$, and $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independently selected from the group consisting of H, halogen, CN, $NO_2$, $C_1$ to $C_3$ alkoxy, $C_1$ to $C_3$ alkyl, and $C_1$ to $C_3$ thioalkyl;

ix) a five or six membered ring having in its backbone 1, 2, or 3 heteroatoms selected from the group consisting of O, S, SO, $SO_2$ and $NR^5$, the five or six membered ring being optionally substituted by one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^F$, and $NR^GCOR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^5$ is H or $C_1$ to $C_3$ alkyl;

W is O or a chemical bond;

or a pharmaceutically acceptable salt thereof; and c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

2. The method according to claim 1 wherein the progestational agent is levonorgestrel and wherein:

$R^4$ is the substituted benzene ring viii) containing the substituents X, Y and Z as shown below:

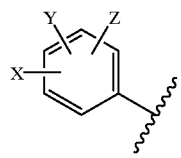

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5-membered heterocyclic ring containing in its backbone 1 to 3 heteroatoms, $COR^D$, $OCOR^D$, and $NR^ECOR^D$; or $R^4$ is the five or six membered ring ix), wherein the five or six membered ring is optionally substituted by one or two independent substituents selected from the group consisting of H, halogen, CN, $NO_2$, $C_1$ to $C_3$ alkyl, and $C_1$ to $C_3$ alkoxy.

3. The method according to claim 1 wherein the progestational agent is levonorgestrel and wherein:

$R_1=R_2$ and are selected from the group consisting of $C_1$ to $C_3$ alkyl and substituted $C_1$ to $C_3$ alkyl, or $R_1$ and $R_2$ are fused to form a carbon-based, saturated 3 to 6 membered spirocyclic ring;

$R^3$ is H, OH, $NH_2$, $C_1$ to $C_6$ alkyl, substituted $C_1$ to $C_6$ alkyl, or $COR^C$;

$R^C$ is H, $C_1$ to $C_3$ alkyl, or $C_1$ to $C_3$ alkoxy;

$R^4$ is (x), (xi), or (xii):

(x) the benzene ring viii) of the structure shown below:

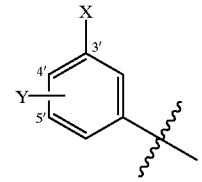

X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring containing in its backbone 1 to 3 heteroatoms, and $C_1$ to $C_3$ thioalkyl;

Y is on the 4' or 5' position and is selected from the group consisting of H, halogen, CN, $NO_2$, $C_1$ to $C_3$ alkoxy, $C_1$ to $C_3$ alkyl, and $C_1$ to $C_3$ thioalkyl;

(xi) the five membered ring ix) of the structure shown below:

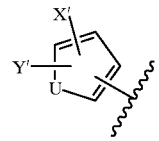

U is O, S, or $NR^5$;

X' is selected from the group consisting of halogen, CN, $NO_2$, $C_1$ to $C_3$ alkyl and $C_1$ to $C_3$ alkoxy;

Y' is H or $C_1$ to $C_3$ alkyl; or (xii) the six membered ring ix) having the structure:

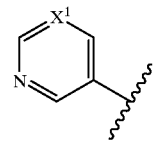

$X^1$ is N or $CX^2$, $X^2$ is halogen, CN or $NO_2$.

4. The method according to claim 1 wherein the progestational agent is levonorgestrel and wherein:

$R_1=R_2$ and are selected from the group consisting of $C_1$ to $C_3$ alkyl and substituted $C_1$ to $C_3$ alkyl, or $R_1$ and $R_2$ are fused to form a carbon-based saturated 3 to 6 membered spirocyclic ring.

5. The method according to claim 1 wherein the progestational agent is levonorgestrel and wherein:

$R_1$ and $R_2$ are fused to form a 3 to 6 membered spirocyclic ring.

6. A method of contraception which comprises administering to a female of child bearing age for 28 consecutive days:

a) a first phase of from 14 to 24 daily dosage units of a progestational agent equal in progestational activity to about 35 to about 100 µg levonorgestrel;

b) a second phase of from 1 to 11 daily dosage units, at a daily dosage of from about 2 to 50 mg, of an antiprogestin compound of the formula:

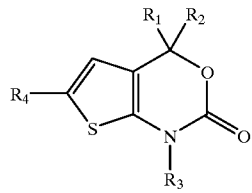

wherein:
$R_1$ and $R_2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkynyl $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^B COR^A$;
or $R_1$ and $R_2$ are fused to form:
  i) a carbon-based saturated 3 to 6 membered spirocyclic ring; or
  ii) a carbon-based 3 to 6 membered spirocyclic ring having one or more carbon-carbon double bonds;
$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or $COR^C$;
$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^B$ is H, $C_1$ to $C_3$ alkyl, or substituted $C_1$ to $C_3$ alkyl;
$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^4$ is a substituted benzene ring containing the substituents X, Y and Z as shown below,

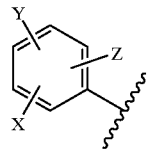

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing in its backbone 1 to 3 heteroatoms, $COR^D$, $OCOR^D$, and $NR^E COR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl; and
Y and Z are independently selected from the group consisting of H, halogen, CN, $NO_2$, $C_1$ to $C_3$ alkoxy, $C_1$ to $C_3$ alkyl, and $C_1$ to $C_3$ thioalkyl;

or a pharmaceutically acceptable salt thereof; and
c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

7. The method according to claim 1 in which the antiprogestin compound is 6-(3-chlorophenyl)-1,4-dihydro-4,4-dimethyl-2H-thieno[2,3-d][1,3]oxazine-2-one, or a pharmaceutically acceptable salt thereof.

8. The method according to claim 1 wherein the progestational agent is selected from the group consisting of levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, and (17-deacetyl) norgestimate.

9. The method according to claim 1 which comprises administering to a female of child bearing age consecutively over a 28 day cycle:
  a) a first phase of 21 daily dosage units of a progestational agent equal in progestational activity to about 35 to about 100 µg levonorgestrel;
  b) a second phase of 3 daily dosage units of an said antiprogestin compound, each daily dosage unit containing said antiprogestin compound at a daily dosage of from about 2 to 50 mg; and
  c) optionally, 4 daily dosage units of an orally and pharmaceutically acceptable placebo to be administered on each day of the 28-day cycle following the first phase and second phase.

10. The method according to claim 1 in which the antiprogestin compound is 6-(3-chlorophenyl)-1,4-dihydro-4,4-dimethyl-2H-thieno[3,2-d][1,3]oxazine-2-one, or a pharmaceutically acceptable salt thereof.

11. A method of contraception which comprises administering to a female of child bearing age for 28 consecutive days:
  a) a first phase of from 14 to 24 daily dosage units of a progestational agent equal in progestational activity to about 35 to about 100 µg levonorgestrel;
  b) a second phase of from 1 to 11 daily dosage units, at a daily dosage of from about 2 to 50 mg, of an antiprogestin compound of the formula:

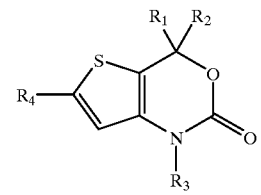

wherein:
$R_1$ and $R_2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to C8 cycloalkyl, substituted $C_3$ to $C_8$ cycloalkyl, aryl, substituted aryl, heterocyclic, substituted heterocyclic, $COR^A$, and $NR^B COR^A$;
or $R_1$ and $R_2$ are fused to form:
  i) a carbon-based saturated 3 to 6 membered spirocyclic ring; or ii) a carbon-based 3 to 6 membered spirocyclic ring having one or more carbon-carbon double bonds;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or $COR^C$;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^C$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is a substituted benzene ring containing the substituents X, Y and Z as shown below,

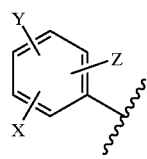

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing in its backbone 1 to 3 heteroatoms, $COR^D$, $OCOR^D$, and $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl; and

Y and Z are independently selected from the group consisting of H, halogen, CN, $NO_2$, $C_1$ to $C_3$ alkoxy, $C_1$ to $C_3$ alkyl, and $C_1$ to $C_3$ thioalkyl;

or a pharmaceutically acceptable salt thereof; and c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

12. A method of contraception which comprises administering to a female of child bearing age for 28 consecutive days:

a) a first phase of from 14 to 24 daily dosage units of a progestational agent equal in progestational activity to about 35 to about 100 µg levonorgestrel;

b) a second phase of from 1 to 11 daily dosage units, at a daily dosage of from about 2 to 50 mg, of an antiprogestin compound of Formula 1:

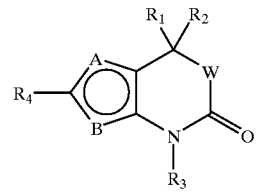

wherein:

A and B are independent substituents selected from the group consisting of S, CH and N;
wherein:
i) when A is S, B is CH or N;
ii) when B is S, A is CH or N;
iii) A and B cannot both be CH; and
iv) when A and B both equal N, one N may be optionally substituted with a $C_1$ to $C_6$ alkyl group;

$R_1$ is selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, substituted aryl, heterocyclic, substituted heterocyclic, $COR^A$, and $NR^8COR^A$ $R_2$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkyl, substituted $C_2$ to $C_6$ alkylaryl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$;

or $R_1$ and $R_2$ are fused to form:
v) an optionally substituted carbon-based, saturated 3 to 8 membered spirocyclic ring;
vi) an optionally substituted carbon-based 3 to 8 membered spirocyclic ring having one or more carbon-carbon double bonds; or
vii) an optionally substituted 3 to 8 membered spirocyclic, heterocyclic ring containing in the backbone one to three heteroatoms selected from the group consisting of O, S and N;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, alkynyl, substituted alkynyl, or $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is vii) or ix):
viii) a substituted benzene ring containing the substituents X, Y and Z as shown below:

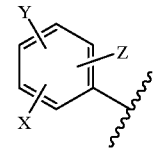

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkyl, substituted $C_1$ to $C_3$ thioalkyl, $C_1$ to $C_3$ aminoalkyl, substituted $C_1$ to $C_3$ aminoalkyl, $NO_2$, $C_1$ to $C_3$ perfluoroalkyl, 5-membered heterocyclic ring containing in its backbone 1 to 3 heteroatoms, $COR^D$, $OCOR^D$, and $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independently selected from the group consisting of H, halogen, CN, $NO_2$, $C_1$ to $C_3$ alkoxy, $C_1$ to $C_3$ alkyl, and $C_1$ to $C_3$ thioalkyl; or ix) a five or six membered ring having in its backbone 1, 2, or 3 heteroatoms selected from the group consisting of O, S, SO, $SO_2$ and $NR^5$, the five or six membered ring being substituted by one or two independent substituents selected from the group consisting of H, halogen, CN, $NO_2$, $C_1$ to $C_3$ alkyl, $C_1$ to $C_3$ alkoxy;

$R^5$ is H or $C_1$ to $C_3$ alkyl;

W is O or a chemical bond;

or a pharmaceutically acceptable salt thereof; and c) optionally a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

13. A method of contraception which comprises administering to a female of child bearing age for 28 consecutive days:
a) a first phase of from 14 to 24 daily dosage units of a progestational agent equal in progestational activity to about 35 to about 100 μg levonorgestrel;
b) a second phase of from 1 to 11 daily dosage units, at a daily dosage of from about 2 to 50 mg, of an antiprogestin compound of Formula 1:

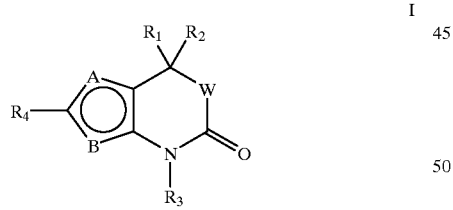

wherein:
A and B are independent substituents selected from the group consisting of S, CH and N; and
i) when A is S, B is CH or N;
ii) when B is S, A is CH or N; and
iii) A and B cannot both be CH;
$R_1$ and $R_2$ are the same and are selected from the group consisting of $C_1$ to $C_3$ alkyl and substituted $C_1$ to $C_3$ alkyl, or $R_1$ and $R_2$ are fused to form a carbon-based, saturated 3 to 6 membered spirocyclic ring;

$R^3$ is H, OH, $NH_2$, $C_1$ to $C_6$ alkyl, substituted $C_1$ to $C_6$ akyl, or $COR^C$;

$R^C$ is H, $C_1$ to $C_4$ alkyl, or $C_1$ to $C_4$ alkoxy;

$R^4$ is (iv), (v) or (vi):

(iv) a substituted benzene ring of the structure shown below:

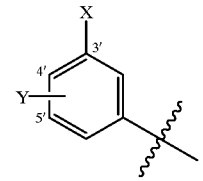

X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring containing in its backbone 1 to 3 heteroatoms, and $C_1$ to $C_3$ thioalkyl;

Y is on the 4' or 5' position and is selected from the group consisting of H, halogen, CN, $NO_2$, $C_1$ to $C_3$ alkoxy, $C_1$ to $C_4$ alkyl, and $C_1$ to $C_3$ thioalkyl; or (v) a five membered ring of the structure shown below:

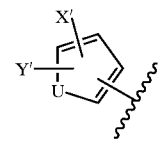

U is O, S, or $NR^5$;

$R^5$ is selected from the group consisting of H, $C_1$ to $C_3$ alkyl, and $C_1$ to $C_4$ $CO_2$ alkyl;

X' is selected from the group consisting of halogen, CN, $NO_2$, $C_1$ to $C_3$ alkyl and $C_1$ to $C_3$ alkoxy;

Y' is H or $C_1$ to $C_4$ alkyl; or (iv) a six-membered ring with the structure:

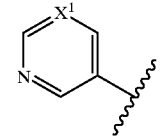

wherein $X^1$ is N or $CX_2$, and $X^2$ is halogen, CN or $NO_2$;

and W is O or a chemical bond;

or a pharmaceutically acceptable salt thereof and c) optionally, a third phase of daily dosage units of an orally and pharmaceutically acceptable placebo for the remaining days of the 28 consecutive days in which no anprogestin, progestin or estrogen is administered; wherein the total daily dosage units of the first, second and third phases equals 28.

* * * * *

UNITED STATES PATENT AND TRADEMARK OFFICE
CERTIFICATE OF CORRECTION

PATENT NO.    : 6,380,178 B1
DATED         : April 30, 2002
INVENTOR(S)   : Gary S. Grubb et al.

It is certified that error appears in the above-identified patent and that said Letters Patent is hereby corrected as shown below:

Column 2,
Lines 50-63, replace the following structure:

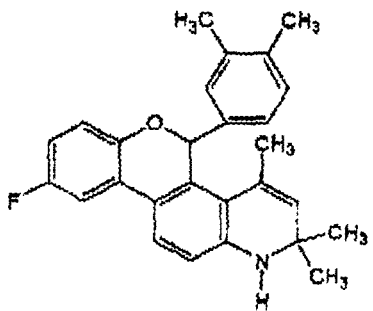

with the following structure:

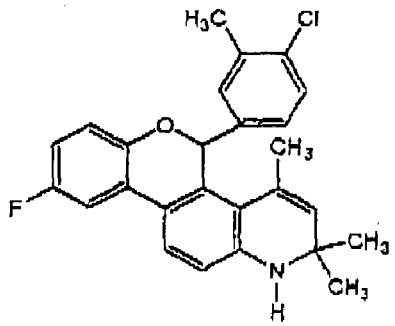

Column 8,
Line 37, replace "Bis" with -- B is --.

Column 10,
Line 34, replace "&yl," with -- aryl, --.

UNITED STATES PATENT AND TRADEMARK OFFICE
CERTIFICATE OF CORRECTION

PATENT NO. : 6,380,178 B1
DATED : April 30, 2002
INVENTOR(S) : Gary S. Grubb et al.

It is certified that error appears in the above-identified patent and that said Letters Patent is hereby corrected as shown below:

Column 13,
Lines 22-33, replace the following structure:

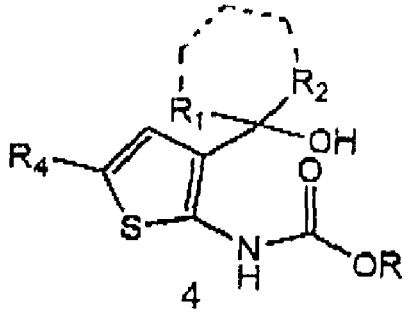

with the following structure:

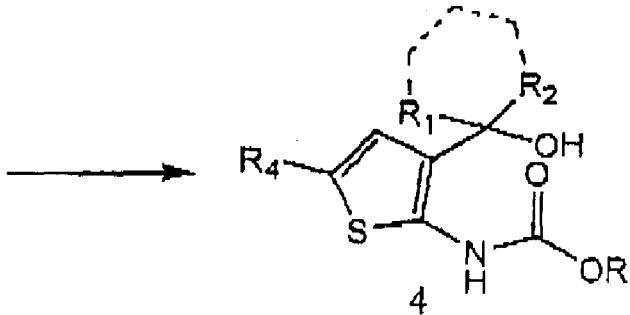

Column 19,
Line 52, replace "drofuran The" with -- drofuran. The --.

Column 25,
Line 59, replace "52" with -- 53 --.

Column 26,
Line 20, replace "TMF" with -- THF --.

Column 28,
Line 16, replace "alkyl" with -- allyl --.

UNITED STATES PATENT AND TRADEMARK OFFICE
CERTIFICATE OF CORRECTION

PATENT NO.    : 6,380,178 B1
DATED         : April 30, 2002
INVENTOR(S)   : Gary S. Grubb et al.

It is certified that error appears in the above-identified patent and that said Letters Patent is hereby corrected as shown below:

Column 29,
Line 33, replace "alkyl" with -- allyl --.
Line 37, replace "etherihexane" with -- ether/hexane --.
Line 39, replace "4.68"4.71" with -- 4.68-4.71 --.
Line 45, replace "methol-ethol-" with -- methyl-ethyl)- --.
Line 46, replace "alkyl ester" with -- allyl ester. --.

Column 30,
Line 24, replace "(keat inactivated)," with -- (heat inactivated), --.

Column 36,
Line 62, replace "C8 cycloalkyl," with -- $C_8$ cycloalkyl, --.

Column 38,
Line 22, replace "cycloalkyl, substituted aryl," with -- cycloalkyl, aryl, substituted aryl --.
Line 24, replace "$NR^8COR^A$" with -- $NR^BCOR^A$ --.
Line 28, replace "alkylaryl," with -- alkynyl --.
Line 54, replace "vii)" with -- viii) --.

Column 40,
Line 60, replace "anprogestin," with -- antiprogestin, --.

Signed and Sealed this

Thirtieth Day of August, 2005

JON W. DUDAS
*Director of the United States Patent and Trademark Office*